US006458574B1

(12) United States Patent
Selden et al.

(10) Patent No.: US 6,458,574 B1
(45) Date of Patent: Oct. 1, 2002

(54) TREATMENT OF A α-GALACTOSIDASE A DEFICIENCY

(75) Inventors: Richard F Selden, Wellesley; Marianne Borowski, Winthrop; Carol M. Kinoshita, Bedford; Douglas A. Treco, Arlington; Melanie D. Williams, Natick; Thomas J. Schuetz, Framingham; Peter F. Daniel, Natick, all of MA (US)

(73) Assignee: Transkaryotic Therapies, Inc., Cambridge, MA (US)

( * ) Notice: Subject to any disclaimer, the term of this patent is extended or adjusted under 35 U.S.C. 154(b) by 0 days.

(21) Appl. No.: 09/266,014

(22) Filed: Mar. 11, 1999

Related U.S. Application Data

(63) Continuation-in-part of application No. 08/928,881, filed on Sep. 12, 1996, now Pat. No. 6,083,725, and a continuation-in-part of application No. PCT/US97/16603, filed on Sep. 12, 1997.
(60) Provisional application No. 60/026,041, filed on Sep. 13, 1996.
(51) Int. Cl.[7] .......................... C12N 9/40; A61K 38/43
(52) U.S. Cl. ................. 435/208; 435/183; 435/193; 536/23.1; 536/23.2; 536/23.4; 424/94.1; 424/94.61
(58) Field of Search ...................... 435/183, 193, 435/208; 536/23.1, 23.2, 23.4; 424/94.1, 94.61

(56) References Cited

U.S. PATENT DOCUMENTS

| | | | |
|---|---|---|---|
| 4,407,957 A | 10/1983 | Lim | 435/178 |
| 4,740,365 A | 4/1988 | Yukimatsu et al. | 424/435 |
| 4,764,376 A | 8/1988 | Hirsch et al. | 514/255 |
| 5,179,023 A | 1/1993 | Calhoun et al. | 435/320.1 |
| 5,356,804 A | 10/1994 | Desnick et al. | 435/208 |
| 5,401,650 A * | 3/1995 | Desnick et al. | 435/208 |
| 5,654,007 A | 8/1997 | Johnson et al. | 424/489 |
| 5,733,761 A | 3/1998 | Treco et al. | 435/172.3 |
| 5,750,376 A | 5/1998 | Weiss et al. | 435/69.2 |
| 5,780,014 A | 7/1998 | Eljamal et al. | 424/46 |
| 5,780,045 A | 7/1998 | McQuinn et al. | 424/439 |
| 5,789,247 A | 8/1998 | Ballay et al. | 435/372.2 |
| 5,798,113 A | 8/1998 | Dionne et al. | 424/422 |
| 5,804,413 A | 9/1998 | DeLuca | 435/69.1 |
| 5,814,607 A | 9/1998 | Patton | 514/12 |
| 5,858,751 A | 1/1999 | Paulson et al. | 435/193 |

FOREIGN PATENT DOCUMENTS

| | | | |
|---|---|---|---|
| WO | WO 90/11353 | 10/1990 | |
| WO | WO 94/12618 | 6/1994 | |
| WO | WO 95/06478 | 3/1995 | |
| WO | WO 98/11206 | 3/1998 | |

OTHER PUBLICATIONS

International Search Report for PCT/US00/06118.
Written Opinion for PCT/US00/06118.
Medin et al., "Correction in trans for Fabry disease: Expression, secretion, and uptake of . . . ", Jul. 1996, Proc.Natl.Acad.Sci.USA, vol. 93; 7917–7922.
Ashwell & Harford, Ann. Rev. Biochem. 51: 531–554 (1982).
Beutler, New Engl. J. Med. 325:1354–1360 (1991).
Bishop et al., J. Biol. Chem. 256: 1307–1316 (1981).
Cuozzo et al., J. Biol. Chem. 273: 21069–21076 (1998).
Delgado et al., Crit. Rev. Ther. Drug Carrier Syst. 9:249–304 (1992).
Diment et al., J. Leukocyte Biol. 42: 485–490 (1987).
Edwards et al., Science 276: 1868–1872 (1997).
Francis et al., Int. J. Hematol. 68(1): 1–18 (1998).
Grammatikos et al., Biotechnol. Progr. 14:410–419 (1998).
Hantzopolous et al., Gene 57:159 (1987).
Herment in et al, Glycobiology 6: 217–230 (1996).
Ihara et al., J. Biochem. (Tokyo) 113: 692–698 (1993).
Ioannou et al., J. Cell Biol. 119: 1137–1150 (1992).
Isidoro et al., Eur. J. Biochem. 191: 591–597 (1990).
Kinstler et al., Pharm. Res. 13: 996–1002 (1996).
Korner et al., Proc. Natl. Acad. Sci. USA 95: 13200–13205 (1998).
Kornfeld & Mellman, Ann. Rev. Cell. Biol. 5: 483–525 (1989).
Kukuruzinska & Lennon, Crit. Rev. Oral. Biol. Med. 9: 415–48 (1998).
LeDonne et al., Arch. Biochem. Biophys. 224: 186 (1983).
Lemansky et al., J. Biol. Chem. 262: 2062 (1987).
Marikar et al., Anal. Biochem. 201: 306–310 (1992).
Matsuura et al., Glycobiology 8: 329–339 (1998).
Mizushima et al., Nucl. Acids Res. 18: 5322 (1990).
Nakano et al., New Engl. J. Med. 333: 288–293 (1995).
Rijcken et al., Biochem.J. 305: 865–870 (1995).
Sburlati et al., Biotechnical. Progr. 14: 189–192 (1998).
Ven der Bliek et al., Cancer Research 48: 5927–5932 (1988).

* cited by examiner

*Primary Examiner*—Rebecca E. Prouty
*Assistant Examiner*—Richard Hutson
(74) *Attorney, Agent, or Firm*—Fish & Richardson PC

(57) ABSTRACT

The invention provides highly purified α-Gal A, and various methods for purifying it; α-Gal A preparations with altered charge and methods for making those preparations; α-Gal A preparations that have an extended circulating half-life in a mammalian host, and methods for making same; and methods and dosages for administering an α-Gal A preparation to a subject.

26 Claims, 9 Drawing Sheets

CTGGGCTGTAGCTATGATAAACCGGCAGGA
GATTGGTGGACCTCGCTCTTATACCATCGCA
GTTGCTTCCCTGGGTAAAGGAGTGGCCTGTA
ATCCTGCCTGCTTCATCACACAGCTCCTCCCT
GTGAAAGGAAGCTAGGGTTCTATGAATGGA
CTTCAAGGTTAAGAAGTCACATAAATCCCAC
AGGCACTGTTTTGCTTCAGCTAGA

Fig. 1

ATTGGTCCGCCCCTGAGGTTAATCTTAAAAG

SacII
CCCAGGTTACCCGCGGAAATTTATGCTGTC

CGGTCACCGTGACAATGCAGCTGAGGAACC

CAGAACTACATCTGGGCTGCGCGCTTGCGCT

TCGCTTCCTGGCCCTCGTTTCCTGGGACATC

CCTGGGGCTAGAGCACTGGACAATGGATTG

NcoI
GCAAGGACGCCTACCATGGGCTGGCTGCAC

TGGGAGCGCTTCATGTGCAACCTTGACTGCC

AGGAAGAGCCAGATTCCTGCATCA

Fig. 2

```
   1 CCGCGGGAAA TTTATGCTGT CCGGTCACCG TGACAATGCA GCTGAGGAAC CCAGAACTAC
  61 ATCTGGGCTG CGCGCTTGCG CTTCGCTTCC TGGCCCTCGT TTCCTGGGAC ATCCCTGGGG
 121 CTAGAGCACT GGACAATGGA TTGGCAAGGA CGCCTACCAT GGGCTGGCTG CACTGGGAGC
 181 GCTTCATGTG CAACCTTGAC TGCCAGGAAG AGCCAGATTC CTGCATCAGT GAGAAGCTCT
 141 TCATGGAGAT GGCAGAGCTC ATGGTCTCAG AAGGCTGGAA GGATGCAGGT TATGAGTACC
 301 TCTGCATTGA TGACTGTTGG ATGGCTCCCC AAAGAGATTC AGAAGGCAGA CTTCAGGCAG
 361 ACCCTCAGCG CTTTCCTCAT GGGATTCGCC AGCTAGCTAA TTATGTTCAC AGCAAAGGAC
 421 TGAAGCTAGG GATTTATGCA GATGTTGGAA ATAAAACCTG CGCAGGCTTC CCTGGGAGTT
 481 TTGGATACTA CGACATTGAT GCCCAGACCT TGCTGACTG GGGAGTAGAT CTGCTAAAAT
 541 TTGATGGTTG TTACTGTGAC AGTTTGGAAA ATTTGGCAGA TGGTTATAAG CACATGTCCT
 601 TGGCCCTGAA TAGGACTGGC AGAAGCATTG TGTACTCCTG TGAGTGGCCT CTTTATATGT
 661 GGCCCTTTCA AAAGCCCAAT TATACAGAAA TCCGACAGTA CTGCAATCAC TGGCGAAATT
 721 TTGCTGACAT TGATGATTCC TGGAAAAGTA TAAAGAGTAT CTTGGACTGG ACATCTTTTA
 781 ACCAGGAGAG AATTGTTGAT GTTGCTGGAC CAGGGGGTTG GAATGACCCA GATATGTTAG
 841 TGATTGGCAA CTTTGGCCTC AGCTGGAATC AGCAAGTAAC TCAGATGGCC CTCTGGGCTA
 901 TCATGGCTGC TCCTTTATTC ATGTCTAATG ACCTCCGACA CATCAGCCCT CAAGCCAAAG
 961 CTCTCCTTCA GGATAAGGAC GTAATTGCCA TCAATCAGGA CCCCTTGGGC AAGCAAGGGT
1021 ACCAGCTTAG ACAGGGAGAC AACTTTGAAG TGTGGGAACG ACCTCTCTCA GGCTTAGCCT
1081 GGGCTGTAGC TATGATAAAC CGGCAGGAGA TTGGTGGACC TCGCTCTTAT ACCATCGCAG
1141 TTGCTTCCCT GGGTAAAGGA GTGGCCTGTA ATCCTGCCTG CTTCATCACA CAGCTCCTCC
1201 CTGTGAAAAG GAAGCTAGGG TTCTATGAAT GGACTTCAAG GTTAAGAAGT CACATAAATC
1261 CCACAGGCAC TGTTTTGCTT CAGCTAGAAA ATACAATGCA GATGTCATTA AAAGACTTAC
1321 TTTAAAAAAA AAAAAAACTC GAG
```

Fig. 3

| | | | | | | | | | | |
|---|---|---|---|---|---|---|---|---|---|---|
| Leu | Asp | Asn | Gly | Leu | Ala | Arg | Thr | Pro | Thr | Met | Gly |
| Trp | Leu | His | Trp | Glu | Arg | Phe | Met | Cys | Asn | Leu | Asp |
| Cys | Gln | Glu | Glu | Pro | Asp | Ser | Cys | Ile | Ser | Glu | Lys |
| Leu | Phe | Met | Glu | Met | Ala | Glu | Leu | Met | Val | Ser | Glu |
| Gly | Trp | Lys | Asp | Ala | Gly | Tyr | Glu | Tyr | Leu | Cys | Ile |
| Asp | Asp | Cys | Trp | Met | Ala | Pro | Gln | Arg | Asp | Ser | Glu |
| Gly | Arg | Leu | Gln | Ala | Asp | Pro | Gln | Arg | Phe | Pro | His |
| Gly | Ile | Arg | Gln | Leu | Ala | Asn | Tyr | Val | His | Ser | Lys |
| Gly | Leu | Lys | Leu | Gly | Ile | Tyr | Ala | Asp | Val | Gly | Asn |
| Lys | Thr | Cys | Ala | Gly | Phe | Pro | Gly | Ser | Phe | Gly | Tyr |
| Tyr | Asp | Ile | Asp | Ala | Gln | Thr | Phe | Ala | Asp | Trp | Gly |
| Val | Asp | Leu | Leu | Lys | Phe | Asp | Gly | Cys | Tyr | Cys | Asp |
| Ser | Leu | Glu | Asn | Leu | Ala | Asp | Gly | Tyr | Lys | His | Met |
| Ser | Leu | Ala | Leu | Asn | Arg | Thr | Gly | Arg | Ser | Ile | Val |
| Tyr | Ser | Cys | Glu | Trp | Pro | Leu | Tyr | Met | Trp | Pro | Phe |
| Gln | Lys | Pro | Asn | Tyr | Thr | Glu | Ile | Arg | Gln | Tyr | Cys |
| Asn | His | Trp | Arg | Asn | Phe | Ala | Asp | Ile | Asp | Asp | Ser |
| Trp | Lys | Ser | Ile | Lys | Ser | Ile | Leu | Asp | Trp | Thr | Ser |
| Phe | Asn | Gln | Glu | Arg | Ile | Val | Asp | Val | Ala | Gly | Pro |
| Gly | Gly | Trp | Asn | Asn | Pro | Asp | Met | Leu | Val | Ile | Gly |
| Asn | Phe | Gly | Leu | Ser | Trp | Asn | Gln | Gln | Val | Thr | Gln |
| Met | Ala | Leu | Trp | Ala | Ile | Met | Ala | Ala | Pro | Leu | Phe |
| Met | Ser | Asn | Asp | Leu | Arg | His | Ile | Ser | Pro | Gln | Ala |
| Lys | Ala | Leu | Leu | Gln | Asp | Lys | Asp | Val | Ile | Ala | Ile |
| Asn | Gln | Asp | Pro | Leu | Gly | Lys | Gln | Gly | Tyr | Gln | Leu |
| Arg | Gln | Gly | Asp | Asn | Phe | Glu | Val | Trp | Glu | Arg | Pro |
| Leu | Ser | Gly | Leu | Ala | Trp | Ala | Val | Ala | Met | Ile | Asn |
| Arg | Gln | Glu | Ile | Gly | Gly | Pro | Arg | Ser | Tyr | Thr | Ile |
| Ala | Val | Ala | Ser | Leu | Gly | Lys | Gly | Val | Ala | Cys | Asn |
| Pro | Ala | Cys | Phe | Ile | Thr | Gln | Leu | Leu | Pro | Val | Lys |
| Arg | Lys | Leu | Gly | Phe | Tyr | Glu | Trp | Thr | Ser | Arg | Leu |
| Arg | Ser | His | Ile | Asn | Pro | Thr | Gly | Thr | Val | Leu | Leu |
| Gln | Leu | Glu | Asn | Thr | Met | Gln | Met | Ser | Leu | Lys | Asp |
| Leu | Leu | | | | | | | | | | |

Fig. 6

```
   1 CTGGACAATG GATTGGCAAG GACGCCTACC ATGGGCTGGC TGCACTGGGA GCGCTTCATG
  61 TGCAACCTTG ACTGCCAGGA AGAGCCAGAT TCCTGCATCA GTGAGAAGCT CTTCATGGAG
 121 ATGGCAGAGC TCATGGTCTC AGAAGGCTGG AAGGATGCAG GTTATGAGTA CCTCTGCATT
 181 GATGACTGTT GGATGGCTCC CCAAAGAGAT TCAGAAGGCA GACTTCAGGC AGACCCTCAG
 241 CGCTTTCCTC ATGGGATTCG CCAGCTAGCT AATTATGTTC ACAGCAAAGG ACTGAAGCTA
 301 GGGATTTATG CAGATGTTGG AAATAAAACC TGCGCAGGCT TCCCTGGGAG TTTTGGATAC
 361 TACGACATTG ATGCCAGAC CTTTGCTGAC TGGGGAGTAG ATCTGCTAAA ATTTGATGGT
 421 TGTTACTGTG ACAGTTTGGA AAATTTGGCA GATGGTTATA AGCACATGTC CTTGGCCCTG
 481 AATAGGACTG GCAGAAGCAT TGTGTACTCC TGTGAGTGGC CTCTTTATAT GTGGCCCTTT
 541 CAAAAGCCCA ATTATACAGA ATCCGACAG TACTGCAATC ACTGGCGAAA TTTTGCTGAC
 601 ATTGATGATT CCTGGAAAAG TATAAAGAGT ATCTTGGACT GGACATCTTT TAACCAGGAG
 661 AGAATTGTTG ATGTTGCTGG ACCAGGGGGT TGGAATGACC CAGATATGTT AGTGATTGGC
 721 AACTTTGGCC TCAGCTGGAA TCAGCAAGTA ACTCAGATGG CCCTCTGGGC TATCATGGCT
 781 GCTCCTTTAT TCATGTCTAA TGACCTCCGA CACATCAGCC CTCAAGCCAA AGCTCTCCTT
 841 CAGGATAAGG ACGTAATTGC CATCAATCAG GACCCCTTGG GCAAGCAAGG GTACCAGCTT
 901 AGACAGGGAG ACAACTTTGA AGTGTGGGAA CGACCTCTCT CAGGCTTAGC CTGGGCTGTA
 961 GCTATGATAA ACCGGCAGGA GATTGGTGGA CCTCGCTCTT ATACCATCGC AGTTGCTTCC
1021 CTGGGTAAAG GAGTGGCCTG TAATCCTGCC TGCTTCATCA CACAGCTCCT CCCTGTGAAA
1081 AGGAAGCTAG GGTTCTATGA ATGGACTTCA AGGTTAAGAA GTCACATAAA TCCCACAGGC
1141 ACTGTTTTGC TTCAGCTAGA AAATACAATG CAGATGTCAT TAAAAGACTT ACTTTAA
```

Fig. 7 ns for the treatment of α-galactosidase A deficiency.

SEQUENCE LISTING

<160> NUMBER OF SEQ ID NOS: 24

<210> SEQ ID NO 1
<211> LENGTH: 210
<212> TYPE: DNA
<213> ORGANISM: Artificial Sequence
<220> FEATURE:
<223> OTHER INFORMATION: Description of Artificial Sequence: Human
      fibroblast library probe: exon 7, including
      amplification primers.

<400> SEQUENCE: 1
ctgggctgta gctatgataa accggcagga gattggtgga cctcgctctt ataccatcgc      60

```
agttgcttcc ctgggtaaag gagtggcctg taatcctgcc tgcttcatca cacagctcct    120
ccctgtgaaa aggaagctag ggttctatga atggacttca aggttaagaa gtcacataaa    180
tcccacaggc actgttttgc ttcagctaga                                     210

<210> SEQ ID NO 2
<211> LENGTH: 268
<212> TYPE: DNA
<213> ORGANISM: Artificial Sequence
<220> FEATURE:
<223> OTHER INFORMATION: Description of Artificial Sequence: 5' end of
      cDNA clone including amplification primers.

<400> SEQUENCE: 2
attggtccgc ccctgaggtt aatcttaaaa gcccaggtta cccgcggaaa tttatgctgt     60
ccggtcaccg tgacaatgca gctgaggaac ccagaactac atctgggctg cgcgcttgcg    120
cttcgcttcc tggccctcgt ttcctgggac atccctgggg ctagagcact ggacaatgga    180
ttggcaagga cgcctaccat gggctggctg cactgggagc gcttcatgtg caaccttgac    240
tgccaggaag agccagattc ctgcatca                                       268

<210> SEQ ID NO 3
<211> LENGTH: 1343
<212> TYPE: DNA
<213> ORGANISM: Homo sapiens

<400> SEQUENCE: 3
ccgcgggaaa tttatgctgt ccggtcaccg tgacaatgca gctgaggaac ccagaactac     60
atctgggctg cgcgcttgcg cttcgcttcc tggccctcgt ttcctgggac atccctgggg    120
ctagagcact ggacaatgga ttggcaagga cgcctaccat gggctggctg cactgggagc    180
gcttcatgtg caaccttgac tgccaggaag agccagattc ctgcatcagt gagaagctct    240
tcatggagat ggcagagctc atggtctcag aaggctggaa ggatgcaggt tatgagtacc    300
tctgcattga tgactgttgg atggctcccc aaagagattc agaaggcaga cttcaggcag    360
accctcagcg ctttcctcat gggattcgcc agctagctaa ttatgttcac agcaaaggac    420
tgaagctagg gatttatgca gatgttggaa ataaaacctg cgcaggcttc cctgggagtt    480
ttggatacta cgacattgat gcccagacct tgctgactgg gggagtagat ctgctaaaat    540
ttgatggttg ttactgtgac agtttggaaa atttggcaga tggttataag cacatgtcct    600
tggccctgaa taggactggc agaagcattg tgtactcctg tgagtggcct ctttatatgt    660
ggccctttca aaagcccaat tatacagaaa tccgacagta ctgcaatcac tggcgaaatt    720
ttgctgacat tgatgattcc tggaaaagta taaagagtat cttggactgg acatctttta    780
accaggagag aattgttgat gttgctggac caggggttg gaatgaccca gatatgttag    840
tgattggcaa ctttggcctc agctggaatc agcaagtaac tcagatggcc ctctgggcta    900
tcatggctgc tcctttattc atgtctaatg acctccgaca catcagccct caagccaaag    960
ctctccttca ggataaggac gtaattgcca tcaatcagga cccttgggc aagcaagggt    1020 accagcttag acagggagac aactttgaag tgtgggaacg acctctctca ggcttagcct    1080
gggctgtagc tatgataaac cggcaggaga ttggtggacc tcgctcttat accatcgcag    1140
ttgcttccct gggtaaagga gtggcctgta atcctgcctg cttcatcaca cagctcctcc    1200
ctgtgaaaag gaagctaggg ttctatgaat ggacttcaag gttaagaagt cacataaatc    1260
ccacaggcac tgttttgctt cagctagaaa atacaatgca gatgtcatta aaagacttac    1320
```

-continued tttaaaaaaa aaaaaaactc gag                                           1343

<210> SEQ ID NO 4
<211> LENGTH: 398
<212> TYPE: PRT
<213> ORGANISM: Homo sapiens

<400> SEQUENCE: 4

Leu Asp Asn Gly Leu Ala Arg Thr Pro Thr Met Gly Trp Leu His Trp
 1               5                  10                  15

Glu Arg Phe Met Cys Asn Leu Asp Cys Gln Glu Glu Pro Asp Ser Cys
            20                  25                  30

Ile Ser Glu Lys Leu Phe Met Glu Met Ala Glu Leu Met Val Ser Glu
        35                  40                  45

Gly Trp Lys Asp Ala Gly Tyr Glu Tyr Leu Cys Ile Asp Asp Cys Trp
 50                  55                  60

Met Ala Pro Gln Arg Asp Ser Glu Gly Arg Leu Gln Ala Asp Pro Gln
 65                  70                  75                  80

Arg Phe Pro His Gly Ile Arg Gln Leu Ala Asn Tyr Val His Ser Lys
                85                  90                  95

Gly Leu Lys Leu Gly Ile Tyr Ala Asp Val Gly Asn Lys Thr Cys Ala
            100                 105                 110

Gly Phe Pro Gly Ser Phe Gly Tyr Tyr Asp Ile Asp Ala Gln Thr Phe
        115                 120                 125

Ala Asp Trp Gly Val Asp Leu Leu Lys Phe Asp Gly Cys Tyr Cys Asp
    130                 135                 140

Ser Leu Glu Asn Leu Ala Asp Gly Tyr Lys His Met Ser Leu Ala Leu
145                 150                 155                 160

Asn Arg Thr Gly Arg Ser Ile Val Tyr Ser Cys Glu Trp Pro Leu Tyr
                165                 170                 175

Met Trp Pro Phe Gln Lys Pro Asn Tyr Thr Glu Ile Arg Gln Tyr Cys
            180                 185                 190

Asn His Trp Arg Asn Phe Ala Asp Ile Asp Asp Ser Trp Lys Ser Ile
        195                 200                 205

Lys Ser Ile Leu Asp Trp Thr Ser Phe Asn Gln Glu Arg Ile Val Asp
    210                 215                 220

Val Ala Gly Pro Gly Gly Trp Asn Asp Pro Asp Met Leu Val Ile Gly
225                 230                 235                 240

Asn Phe Gly Leu Ser Trp Asn Gln Gln Val Thr Gln Met Ala Leu Trp
                245                 250                 255

Ala Ile Met Ala Ala Pro Leu Phe Met Ser Asn Asp Leu Arg His Ile
            260                 265                 270

Ser Pro Gln Ala Lys Ala Leu Leu Gln Asp Lys Asp Val Ile Ala Ile
        275                 280                 285

Asn Gln Asp Pro Leu Gly Lys Gln Gly Tyr Gln Leu Arg Gln Gly Asp
    290                 295                 300

Asn Phe Glu Val Trp Glu Arg Pro Leu Ser Gly Leu Ala Trp Ala Val
305                 310                 315                 320

Ala Met Ile Asn Arg Gln Glu Ile Gly Gly Pro Arg Ser Tyr Thr Ile
                325                 330                 335

Ala Val Ala Ser Leu Gly Lys Gly Val Ala Cys Asn Pro Ala Cys Phe
            340                 345                 350

Ile Thr Gln Leu Leu Pro Val Lys Arg Lys Leu Gly Phe Tyr Glu Trp
        355                 360                 365

```
Thr Ser Arg Leu Arg Ser His Ile Asn Pro Thr Gly Thr Val Leu Leu
    370                 375                 380

Gln Leu Glu Asn Thr Met Gln Met Ser Leu Lys Asp Leu Leu
385                 390                 395
```

<210> SEQ ID NO 5
<211> LENGTH: 1197
<212> TYPE: DNA
<213> ORGANISM: Homo sapiens

<400> SEQUENCE: 5

```
ctggacaatg gattggcaag gacgcctacc atgggctggc tgcactggga gcgcttcatg      60
tgcaaccttg actgccagga agagccagat tcctgcatca gtgagaagct cttcatggag     120
atggcagagc tcatggtctc agaaggctgg aaggatgcag gttatgagta cctctgcatt     180
gatgactgtt ggatggctcc ccaaagagat tcagaaggca gacttcaggc agaccctcag     240
cgctttcctc atgggattcg ccagctagct aattatgttc acagcaaagg actgaagcta     300
gggatttatg cagatgttgg aaataaaacc tgcgcaggct tccctgggag ttttggatac     360
tacgacattg atgcccagac ctttgctgac tggggagtag atctgctaaa atttgatggt     420
tgttactgtg acagtttgga aaatttggca gatggttata agcacatgtc cttggccctg     480
aataggactg gcagaagcat tgtgtactcc tgtgagtggc ctctttatat gtggcccttt     540
caaaagccca attatacaga aatccgacag tactgcaatc actggcgaaa ttttgctgac     600
attgatgatt cctggaaaag tataaagagt atcttggact ggacatcttt taaccaggag     660
agaattgttg atgttgctgg accagggggt tggaatgacc cagatatgtt agtgattggc     720
aactttggcc tcagctggaa tcagcaagta actcagatgg ccctctgggc tatcatggct     780
gctcctttat tcatgtctaa tgacctccga cacatcagcc ctcaagccaa agctctcctt     840
caggataagg acgtaattgc catcaatcag gaccccttgg gcaagcaagg gtaccagctt     900
agacagggag acaactttga agtgtgggaa cgacctctct caggcttagc ctgggctgta     960
gctatgataa accggcagga gattggtgga cctcgctctt ataccatcgc agttgcttcc    1020
ctgggtaaag gagtggcctg taatcctgcc tgcttcatca cacagctcct ccctgtgaaa    1080
aggaagctag ggttctatga atggacttca aggttaagaa gtcacataaa tcccacaggc    1140
actgttttgc ttcagctaga aaatacaatg cagatgtcat taaaagactt actttaa      1197
```

<210> SEQ ID NO 6
<211> LENGTH: 22
<212> TYPE: DNA
<213> ORGANISM: Artificial Sequence
<220> FEATURE:
<223> OTHER INFORMATION: Description of Artificial Sequence: PCR Primer

<400> SEQUENCE: 6

```
ctgggctgta gctatgataa ac                                                22
```

<210> SEQ ID NO 7
<211> LENGTH: 21
<212> TYPE: DNA
<213> ORGANISM: Artificial Sequence
<220> FEATURE:
<223> OTHER INFORMATION: Description of Artificial Sequence: PCR Primer

<400> SEQUENCE: 7

```
tctagctgaa gcaaaacagt g                                                 21
```

```
<210> SEQ ID NO 8
<211> LENGTH: 19
<212> TYPE: DNA
<213> ORGANISM: Artificial Sequence
<220> FEATURE:
<223> OTHER INFORMATION: Description of Artificial Sequence: PCR Primer

<400> SEQUENCE: 8
attggtccgc ccctgaggt                                                19

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: PCR Primer

<400> SEQUENCE: 9
tgatgcagga atctggctct                                               20

<210> SEQ ID NO 10
<211> LENGTH: 35
<212> TYPE: DNA
<213> ORGANISM: Artificial Sequence
<220> FEATURE:
<223> OTHER INFORMATION: Description of Artificial Sequence: PCR Primer

<400> SEQUENCE: 10
ttttggatcc ctcgaggaca ttgattattg actag                              35

<210> SEQ ID NO 11
<211> LENGTH: 28
<212> TYPE: DNA
<213> ORGANISM: Artificial Sequence
<220> FEATURE:
<223> OTHER INFORMATION: Description of Artificial Sequence: PCR Primer

<400> SEQUENCE: 11
ttttggatcc cgtgtcaagg acggtgac                                      28

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: PCR Primer

<400> SEQUENCE: 12
ttttggatcc accatggcta                                               20

<210> SEQ ID NO 13
<211> LENGTH: 24
<212> TYPE: DNA
<213> ORGANISM: Artificial Sequence
<220> FEATURE:
<223> OTHER INFORMATION: Description of Artificial Sequence: PCR Primer

<400> SEQUENCE: 13
ttttgccggc actgccctct tgaa                                          24

<210> SEQ ID NO 14
<211> LENGTH: 24
<212> TYPE: DNA
<213> ORGANISM: Artificial Sequence
<220> FEATURE:
<223> OTHER INFORMATION: Description of Artificial Sequence: PCR Primer
```

<400> SEQUENCE: 14
ttttcagctg gacaatggat tggc                                    24

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence: PCR Primer

<400> SEQUENCE: 15
ttttgctagc tggcgaatcc                                         20

<210> SEQ ID NO 16
<211> LENGTH: 30
<212> TYPE: DNA
<213> ORGANISM: Artificial Sequence
<220> FEATURE:
<223> OTHER INFORMATION: Description of Artificial Sequence: PCR Primer

<400> SEQUENCE: 16
ttttggatcc gtgtcccata gtgtttccaa                              30

<210> SEQ ID NO 17
<211> LENGTH: 28
<212> TYPE: DNA
<213> ORGANISM: Artificial Sequence
<220> FEATURE:
<223> OTHER INFORMATION: Description of Artificial Sequence: PCR Primer

<400> SEQUENCE: 17
ttttggatcc gcagtcgtgg ccagtacc                                28

<210> SEQ ID NO 18
<211> LENGTH: 12
<212> TYPE: DNA
<213> ORGANISM: Artificial Sequence
<220> FEATURE:
<223> OTHER INFORMATION: Description of Artificial Sequence: Insertion
      Oligo

<400> SEQUENCE: 18
ctagtcctag ga                                                 12

<210> SEQ ID NO 19
<211> LENGTH: 22
<212> TYPE: DNA
<213> ORGANISM: Artificial Sequence
<220> FEATURE:
<223> OTHER INFORMATION: Description of Artificial Sequence: PCR Primer

<400> SEQUENCE: 19
ttttgagcac agagcctcgc ct                                      22

<210> SEQ ID NO 20
<211> LENGTH: 30
<212> TYPE: DNA
<213> ORGANISM: Artificial Sequence
<220> FEATURE:
<223> OTHER INFORMATION: Description of Artificial Sequence: Partial
      Collagen Promoter

<400> SEQUENCE: 20
ttttggatcc ggtgagctgc gagaatagcc                              30

```
<210> SEQ ID NO 21
<211> LENGTH: 76
<212> TYPE: DNA
<213> ORGANISM: Artificial Sequence
<220> FEATURE:
<223> OTHER INFORMATION: Description of Artificial Sequence: Partial
      Collagen Promoter

<400> SEQUENCE: 21
gggcccccag ccccagccct cccattggtg gaggcccttt tggaggcacc ctagggccag        60
gaaacttttg ccgtat                                                       76

<210> SEQ ID NO 22
<211> LENGTH: 69
<212> TYPE: DNA
<213> ORGANISM: Artificial Sequence
<220> FEATURE:
<223> OTHER INFORMATION: Description of Artificial Sequence: Partial
      Collagen Promoter

<400> SEQUENCE: 22
aaatagggca gatccgggct ttattatttt agcaccacgg ccgccgagac cgcgtccgcc        60
ccgcgagca                                                               69

<210> SEQ ID NO 23
<211> LENGTH: 86
<212> TYPE: DNA
<213> ORGANISM: Artificial Sequence
<220> FEATURE:
<223> OTHER INFORMATION: Description of Artificial Sequence: Partial
      Collagen promoter

<400> SEQUENCE: 23
tgccctattt atacggcaaa agtttcctgg ccctagggtg cctccaaaag ggcctccacc        60
aatgggaggg ctggggctgg gggccc                                            86

<210> SEQ ID NO 24
<211> LENGTH: 55
<212> TYPE: DNA
<213> ORGANISM: Artificial Sequence
<220> FEATURE:
<223> OTHER INFORMATION: Description of Artificial Sequence: PCR Primer

<400> SEQUENCE: 24
cgcggggcgg acgcggtctc ggcggccgtg gtgctaaaat aataaagccc ggatc            55
```

TREATMENT OF A α-GALACTOSIDASE A DEFICIENCY

RELATED APPLICATIONS

The present application is a continuation-in-part of U.S. Ser. No. 08/928,881, filed on Sep. 12, 1996, now U.S. Pat. No. 6,083,725 and PCT/US97/16603, filed on Sep. 12, 1997, which claims the benefit of Ser. No. 60/026,041, filed Sep. 13, 1996 which are incorporated herein by reference.

FIELD OF THE INVENTION

The present invention relates to methods and compositions for the treatment of α-galactosidase A deficiency.

BACKGROUND OF THE INVENTION

Fabry disease is an X-linked inherited lysosomal storage disease characterized by severe renal impairment, angiokeratomas, and cardiovascular abnormalities, including ventricular enlargement and mitral valve insufficiency. Fabry disease also affects the peripheral nervous system, causing episodes of agonizing, burning pain in the extremities. Fabry disease is caused by a deficiency in the enzyme α-galactosidase A (α-Gal A). α-Gal A is the lysosomal glycohydrolase that cleaves the terminal α-galactosyl moieties of various glycoconjugates. Fabry disease results in a blockage of the catabolism of the neutral glycosphingolipid, ceramide trihexoside (CTH), and accumulation of this enzyme substrate within cells and in the bloodstream.

Due to the X-linked inheritance pattern of the disease, most Fabry disease patients are male. Although severely affected female heterozygotes have been observed, female heterozygotes are often asymptomatic or have relatively mild symptoms (such as a characteristic opacity of the cornea). An atypical variant of Fabry disease, exhibiting low residual α-Gal A activity and either very mild symptoms or apparently no other symptoms characteristic of Fabry disease, correlates with left ventricular hypertrophy and cardiac disease. Nakano et al., *New Engl. J. Med.* 333: 288–293 (1995). A reduction in α-Gal A may be the cause of such cardiac abnormalities.

The cDNA and gene encoding human α-Gal A have been isolated and sequenced. Human α-Gal A is expressed as a 429-amino acid polypeptide, of which the N-terminal 31 amino acids are the signal peptide. The human enzyme has been expressed in Chinese Hamster Ovary (CHO) cells (Desnick et al., U.S. Pat. No. 5,356,804; Ioannou et al., *J. Cell Biol.* 119: 1137 (1992)); and insect cells (Calhoun et al., WO 90/11353).

However, current preparations of α-Gal A have limited efficacy. Methods for the preparation of α-Gal A with relatively high purity depend on the use of affinity chromatography, using a combination of lectin affinity chromatography (concanavalin A (Con A) Sepharose®) and affinity chromatography based on binding of α-Gal A to the substrate analog N-6-aininohexanoyl-α-D-galactosylamine coupled to a Sepharose® matrix. See, e.g., Bishop et al., *J. Biol. Chem.* 256: 1307–1316 (1981). The use of proteinaceous lectin affinity resins and substrate analog resins is typically associated with the continuous leaching of the affinity agent from the solid support (Marikar et al., *Anal. Biochem.* 201: 306–310 (1992), resulting in contamination of the purified product with the affinity agent either free in solution or bound to eluted protein. Such contaminants make the product unsuitable for use in pharmaceutical preparations. Bound substrate analogs and lectins can also have substantial negative effects on the enzymatic, functional, and structural properties of proteins. Moreover, α-Gal A produced by the methods in the prior art is rapidly eliminated by the liver.

Thus, a need remains in the art for a purification protocol using conventional chromatography resins, which are readily available in supplies and quality suitable for large-scale commercial use, and which produces an α-Gal A preparation that is free of affinity agent. In addition, a need remains in the art for α-Gal A preparations with an increased circulating half-life and increased uptake in specific tissues other than liver.

SUMMARY OF THE INVENTION

The invention provides highly purified α-Gal A preparations, and various methods for purifying the α-Gal A glycoforms. The invention also provides α-Gal A preparations with altered charge and methods for making those preparations. Charge alterations are achieved by increasing the sialic acid content of α-Gal A and/or by increasing the phosphorylation of α-Gal A. The invention further provides α-Gal A preparations that have an extended circulating half-life in a mammalian host, and methods for making same. Finally, the present invention further provides methods and dosages for administering an α-Gal A preparation to a subject. The α-Gal A preparations of the present invention will be useful for treatment of individuals with Fabry disease or atypical variants of Fabry disease, e.g., specific populations of Fabry patients with predominantly cardiovascular abnormalities, such as ventricular enlargement, e.g., left ventricular hypertrophy (LVH), and/or mitral valve insufficiency, or Fabry patients with predominantly renal involvement.

BRIEF DESCRIPTION OF THE DRAWINGS

FIG. 1 is a representation of the 210 bp probe that was used to isolate an α-Gal A cDNA from a human fibroblast cDNA library (SEQ ID NO:1). The sequence is from exon 7 of the α-Gal A gene. The probe was isolated from human genomic DNA by the polymerase chain reaction (PCR). The regions underlined in the figure correspond to the sequences of the amplification primers.

FIG. 2 is a representation of the sequence of the DNA fragment that completes the 5' end of the α-Gal A cDNA clone (SEQ ID NO:2). This fragment was amplified from human genomic DNA by PCR. The regions underlined correspond to the sequences of the amplification primers. The positions of the NcoI and SacII restriction endonuclease sites, which were used for subcloning as described in Example 1, are also shown.

FIG. 3 is a representation of the sequence of α-Gal A cDNA, including the sequence that encodes the signal peptide (SEQ ID NO:3).

FIG. 6 is a representation of the human α-Gal A amino acid sequence (SEQ ID NO:4).

FIG. 7 is a representation of the cDNA sequence encoding human α-Gal A (without signal peptide) (SEQ ID NO:5).

DETAILED DESCRIPTION OF THE INVENTION

Introduction

Figure 4:
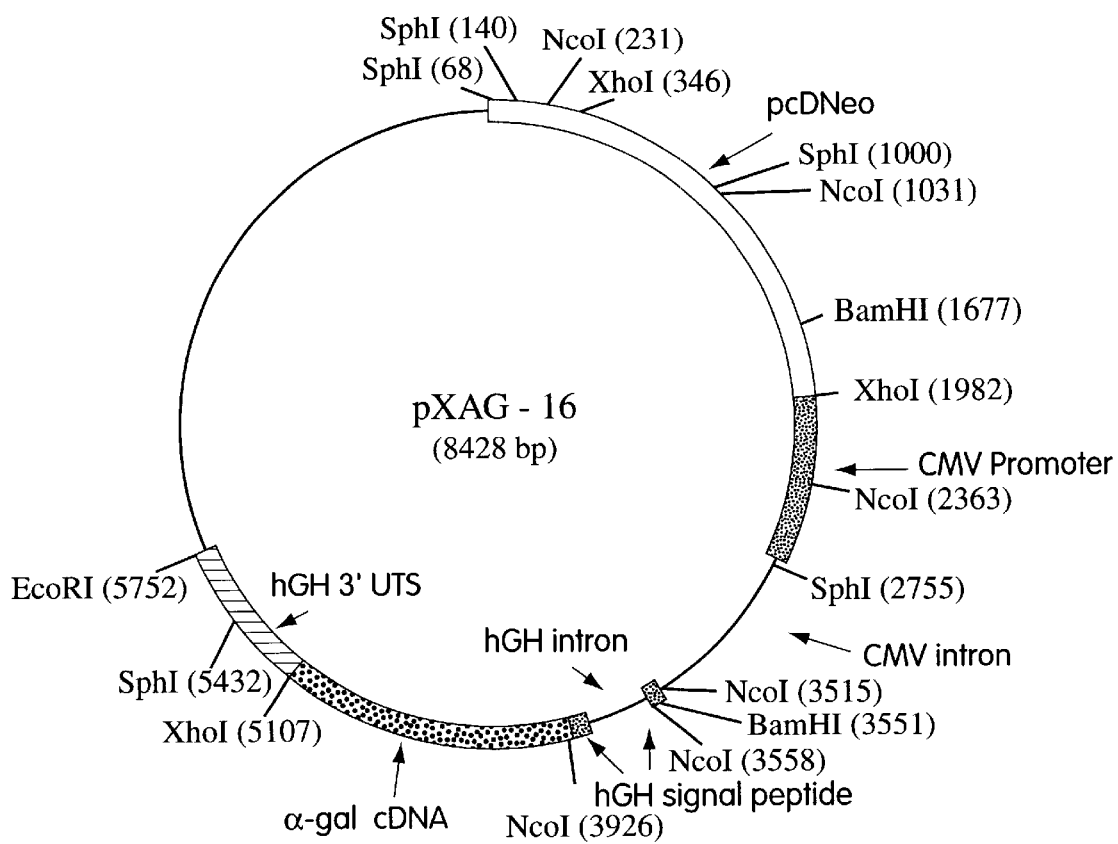
FIG. 4 is a schematic map of pXAG-16, an α-Gal A expression construct that includes the CMV (cytomegalovirus) promoter, exon 1, and first intron, the hGH signal peptide coding sequence and first intron, the cDNA for α-Gal A (lacking the α-Gal A signal peptide sequence) and the hGH 3' UTS. pcDNeo indicates the position of the neo gene derived from plasmid pcDNeo.

The invention described herein relates to certain novel α-Gal A preparations and methods for making them, as well as methods for treating patients with Fabry disease or atypical variants of Fabry disease using those preparations. Certain contemplated representative embodiments are summarized and described in greater detail below.

The invention uses α-Gal A produced in any cell (an α-Gal A production cell) for the treatment of Fabry disease. In a preferred embodiment, the invention uses human α-Gal A produced using standard genetic engineering techniques (based on introduction of the cloned α-Gal A gene or cDNA into a host cell), or gene activation.

The invention provides preparations, and methods for making same, that contain a higher purity α-Gal A than prepared in the prior art. Using the purification methods of the present invention, compositions of human α-Gal A preparations are preferably purified to at least 98% homogeneity, more preferably to at least 99% homogeneity, and most preferably to at least 99.5% homogeneity, as measured by SDS-PAGE or reverse phase HPLC. The specific activity of the α-Gal A preparations of the present invention is preferably at least $2.0 \times 10^6$ units/mg protein, more preferably at least $3.0 \times 10^6$ units/mg protein, and most preferably at least $3.5 \times 10^6$ units/mg protein.

In one embodiment, α-Gal A preparation is purified by separating the various glycoforms of α-Gal A from other components on a hydrophobic interaction resin, but does not include a lectin chromatography step. In a preferred embodiment, the functional moiety of the hydrophobic interaction resin includes a butyl group.

In an alternative embodiment, α-Gal A preparation is purified by first binding the various glycoforms of α-Gal A to a cation exchange resin in a column at acidic pH in an equilibration buffer. The column is then washed with the equilibration buffer to elute the unbound material, and the various glycoforms of α-Gal A are eluted using, as an elution solution, a salt solution of 10–100 mM, a buffered solution of pH 4–5, or a combination thereof. In a preferred embodiment, the equilibration buffer has a pH of about 4.4.

In another alternative embodiment, α-Gal A preparation is purified by separating the various glycoforms of α-Gal A in a sample from the other components in the sample using a purification procedure comprising a step of at least one of chromatofocusing chromatography, metal chelate affinity chromatography, or immunoaffinity chromatography as a purification procedure.

The invention further provides α-Gal A preparations and methods for making α-Gal A preparations that have α-Gal A with altered charge. The preparations may include different glycoforms of α-Gal A. Charge alterations are achieved by increasing the sialic acid content of α-Gal A preparations and/or by increasing the phosphorylation of α-Gal A preparations.

The sialic acid content of α-Gal A preparations is increased by (i) isolation of the highly charged and/or higher molecular weight α-Gal A glycoforms during or after the purification process; (ii) adding sialic acid residues using cells genetically modified (either by conventional genetic engineering methods or gene activation) to express a sialyl transferase gene or cDNA; or (iii) fermentation or growth of cells expressing the enzyme in a low ammonium environment.

The phosphorylation of α-Gal A preparations is increased by (i) adding phosphate residues using cells genetically modified (either by conventional genetic engineering methods or gene activation) to express a phosphoryl transferase gene or cDNA; or (ii) adding phosphatase inhibitors to the cultured cells.

Using the methods of the present invention, human glycosylated α-Gal A preparations are obtained, wherein between 35% and 85% of the oligosaccharides are charged. In a preferred embodiment, at least 35% of the oligosaccharides are charged. In a more preferred embodiment, at least 50% of the oligosaccharides are charged.

Alternative preferred human glycosylated α-Gal A preparations have multiple α-Gal A glycoforms with preferably at least 20%, more preferably at least 50%, and most preferably at least 70% complex glycans with 2–4 sialic acid residues. In an alternative preferred embodiment, human glycosylated α-Gal A preparations with multiple glycoforms have an oligosaccharide charge, as measured by the Z number, greater than 100, preferably greater than 150, and more preferably greater than 170. In another alternative preferred embodiment, human glycosylated α-Gal A preparations with multiple glycoforms have at least on average between 16–50%, preferably 25–50%, more preferably at least 30%, of glycoforms being phosphorylated. In another alternative embodiment, the preparations with multiple glycoforms have between 50–75%, preferably 60%, of the total glycans being sialylated.

In one embodiment of the present invention, a glycosylated α-Gal A preparation having an increased oligosaccharide charge is produced by first introducing a polynucleotide, which encodes for GlcNAc transferase III (GnT-III), into an α-Gal A production cell, or introducing a regulatory sequence by homologous recombination that regulates expression of an endogenous GnT-III gene. The α-Gal A production cell is then cultured under culture conditions which results in expression of α-Gal A and GnT-III. The final step consists of isolating the α-Gal A preparation with increased oligosaccharide charge.

In an alternative embodiment of the present invention, a glycosylated α-Gal A preparation having an increased oligosaccharide charge is produced by first introducing a polynucleotide, which encodes for a sialyl transferase, into an α-Gal A production cell, or introducing a regulatory sequence by homologous recombination that regulates expression of an endogenous sialyl transferase gene. The α-Gal A production cell is then cultured under culture conditions which results in expression of α-Gal A and the sialyl transferase. The final step consists of isolating the α-Gal A preparation with increased oligosaccharide charge. Preferred sialyl transferases include an a2,3-sialyl transferase and an α2,6-sialyl transferase. In a preferred embodiment, this method includes the additional step of selecting for α-Gal A glycoforms with increased size or increase charge by fractionation or purification of the preparation.

In another embodiment, a glycosylated α-Gal A preparation with increased sialylation is obtained by contacting an α-Gal A production cell with a culture medium having an ammonium concentration below 10 mM, more preferably below 2 mM. In a preferred embodiment, the low ammonium environment is achieved by addition of glutamine synthetase to the culture medium. In an alternative preferred embodiment, the low ammonium environment is achieved by continuous or intermittent perfusion of the α-Gal A production cell with fresh culture medium to maintain the ammonium concentration below 10 mM, more preferably below 2 mM.

In yet another embodiment, a glycosylated α-Gal A preparation with increased phosphorylation is obtained by first introducing into an α-Gal A production cell a polynucleotide which encodes for phosphoryl transferase, or by introducing a regulatory sequence by homologous recombination that regulates expression of an endogenous phosphoryl transferase gene. The α-Gal A production cell is then cultured under culture conditions which results in expression of α-Gal A and phosphoryl transferase. The α-Gal A preparation with increased phosphorylation compared to the α-Gal A produced in a cell without the polynucleotide is then isolated. In a preferred embodiment, the α-Gal A preparations produced by the methods of the present invention have multiple glycoforms with between 16–50%, preferably 25–50%, more preferably at least 30%, of glycoforms being phosphorylated. In a preferred embodiment, this method includes the additional step of selecting for α-Gal A glycoforms with increased size or increase charge by fractionation or purification of the preparation.

In still another embodiment, a glycosylated α-Gal A preparation with increased phosphorylation is obtained by adding a phosphatase inhibitor, e.g., bromotetramisole, to cultured cells. Low levels of bovine plasma alkaline phosphatase can be present in the fetal calf serum used as a growth additive for cultured cells. This raises the possibility that exposed Man-6-P epitopes on secreted α-Gal A could be a substrate for serum alkaline phosphatase. Bromotetramisole has been shown to be a potent inhibitor of alkaline phosphatase; Ki=2.8 mM (Metaye et al., *Biochem. Pharmacol.* 15: 4263–4268 (1988)) and complete inhibition is achieved at a concentration of 0.1 mM (Borgers & Thone, *Histochemistry* 44: 277–280 (1975)). Therefore, a phosphatase inhibitor, e.g., bromotetramisole can be added to cultured cells in one embodiment to maximize the high-uptake form of α-Gal A present in the culture medium by preventing hydrolysis of the Man-6-P ester groups.

The invention further provides α-Gal A preparations, and methods for making same, that have an extended circulating half-life in a mammalian host. The circulating half-life and cellular uptake is enhanced by (i) increasing the sialic acid content of α-Gal A (achieved as above); (ii) increasing the phosphorylation of α-Gal A (achieved as above); (iii) PEGylation of α-Gal A; or (iv) sequential removal of the sialic acid and terminal galactose residues, or removal of terminal galactose residues, on the oligosaccharide chains on α-Gal A.

Improved sialylation of α-Gal A preparations enhances the circulatory half-life of exogenous α-Gal A. In addition, improved sialylation of α-Gal A improves its uptake, relative to that of hepatocytes, in non-hepatocytes such as liver endothelial cells, liver sinusoidal cells, pulmonary cells, renal cells, neural cells, endothelial cells, or cardiac cells. The human glycosylated α-Gal A preparation with increased sialic acid content preferably includes multiple glycoforms, with at least 20% complex glycans having 2–4 sialic acid residues. An alternative preferred human glycosylated α-Gal A preparation has multiple glycoforms, wherein between 50–75%, preferably at least 60%, of the total glycans are sialylated.

Phosphorylation of α-Gal A preparations also improves the level of α-Gal A entering cells. The phosphorylation occurs within the cells expressing the α-Gal A. One preferred human glycosylated α-Gal A preparation of the present invention preferably includes multiple glycoforms with at least on average between 16–50%, preferably 25–50%, more preferably at least 30%, of the glycoforms, being phosphorylated.

In an alternate embodiment, the circulatory half-life of a human α-Gal A preparation is enhanced by complexing α-Gal A with polyethylene glycol. In a preferred embodiment, the α-Gal A preparation is complexed using tresyl monomethoxy PEG (TMPEG) to form a PEGylated-α-Gal A. The PEGylated-α-Gal A is then purified to provide an isolated, PEGylated-α-Gal A preparation. PEGylation of α-Gal A increases the circulating half-life and in vivo efficacy of the protein.

Sialylation affects the circulatory half-life and biodistribution of proteins. Proteins with minimal or no sialic acid are readily internalized by the asialoglycoprotein receptor (Ashwell receptor) on hepatocytes by exposed galactose residues on the protein. The circulating half-life of galactose-terminated α-Gal A can be enhanced by sequentially (1) removing sialic acid by contacting α-Gal A with neuraminidase (sialidase), thereby leaving the terminal galactose moieties exposed, and (2) removing the terminal galactoside residues by contacting the desialylated α-Gal A with β-galactosidase. The resulting α-Gal A preparation has a reduced number of terminal sialic acid and/or terminal galactoside residues on the oligosaccharide chains compared to (α-Gal A preparations not sequentially contacted with neuraminidase and β-galactosidase. Alternatively, the circulating half-life of galactose-terminated α-Gal A can be enhanced by only removing the terminal galactoside residues by contacting the desialylated α-Gal A with β-galactosidase. The resulting α-Gal A preparation has a reduced number of terminal galactoside residues on the oligosaccharide chains compared to α-Gal A preparations not contacted with β-galactosidase. In a preferred embodiment, following sequential contact with neuraminidase and β-galactosidase, the resulting α-Gal A preparations are subsequently contacted with β-hexosaminidase, thereby cleaving the oligosaccharide to the trimannose core.

In addition, sialylation levels can vary depending on the cell type used. Therefore, in another preferred embodiment, sialylation of α-Gal A can be enhanced by screening for mammalian cells, e.g., human cells, that have relatively high sialyl transferase activity and using such cells as α-Gal A production cells.

The invention further provides formulations of an α-Gal A preparation that are substantially free of non-α-Gal A proteins, such as albumin, non-α-Gal A proteins produced by the host cell, or proteins isolated from animal tissue or fluid. In one embodiment, the formulation further comprises an excipient. Preferred excipients include mannitol, sorbitol, glycerol, amino acids, lipids, EDTA, EGTA, sodium chloride, polyethylene glycol, polyvinylpyrollidone, dextran, or combinations of any of these excipients. In another embodiment, the formulation further comprises a non-ionic detergent. Preferred non-ionic detergents include Polysorbate 20, Polysorbate 80, Triton X-100, Triton X-114, Nonidet P-40, Octyl a-glucoside, Octyl b-glucoside, Brij 35, Pluronic, and Tween 20. In a preferred embodiment, the non-ionic detergent comprises Polysorbate 20 or Polysorbate 80. A preferred formulation further comprises phosphate-buffered saline, preferably at pH 6.

The present invention further provides methods for administering an α-Gal A preparation to a subject. In a preferred embodiment, the α-Gal A preparation is an α-Gal A preparation with altered charge, e.g., increased oligosaccharide charge, and/or extended circulating half-life as described herein. The dose of administration is preferably between 0.05–5.0 mg, more preferably between 0.1–0.3 mg, of the α-Gal A preparation per kilogram body weight weekly or biweekly. In a preferred embodiment, the dose of administration is about 0.2 mg per kilogram body weight biweekly. In these methods, the dose can be administered intramuscularly, orally, rectally, subcutaneously, intra-arterially, intraperitoneally, intracerebrally, intranasally, intradermally, intrathecally, transmucosally, transdermally, or via inhalation. In one embodiment, the method for delivering α-Gal A preparation to a subject comprises subcutaneously administering a dose ranging between 0.01–10.0 mg, preferably 0.1–5.0 mg, of the α-Gal A preparation per kg body weight biweekly or weekly. The α-Gal A preparation can also be administered intravenously, e.g., in a intravenous bolus injection, in a slow push intravenous injection, or by continuous intravenous injection. In any of the above methods, the α-Gal A preparation can be delivered using a delivery system such as pump delivery, encapsulated cell delivery, liposomal delivery, needle-delivered injection, needle-less injection, nebulizer, aeorosolizer, electroporation, and transdermal patch. Any of the α-Gal A preparation described above can be administered by these methods.

An individual who is suspected of having, or known to have, Fabry disease may be treated by administration of the α-Gal A preparation described above, using the above-described methods of administration and doses. The present invention contemplates treatment of individuals with Fabry disease generally ("Fabry patients"), as well as atypical variants of Fabry disease, e.g., specific populations of Fabry patients with predominantly cardiovascular abnormalities, defined here as Fabry patients with ventricular enlargement, e.g., left ventricular hypertrophy (LVH), and/or mitral valve insufficiency, or Fabry patients with predominantly renal involvement.

α-Gal A

α-Gal A is a homodimeric glycoprotein that hydrolyses the terminal α-galactosyl moieties from glycolipids and glycoproteins.

The terms mature "α-Gal A" and "GA-GAL" and "SEQ ID NO:5" (see FIG. 7) refer to α-Gal A without a signal peptide (for α-Gal A with the signal peptide, see FIG. 3 and SEQ ID NO:3). The term "α-Gal A preparation," as defined herein, is used interchangeably with the term "glycosylated α-Gal A preparation" and comprises various glycosylated α-Gal A glycoforms.

A "signal peptide" is a peptide sequence that directs a newly synthesized polypeptide to which the signal peptide is attached to the endoplasmic reticulum (ER) for further post-translational processing and distribution.

An "heterologous signal peptide," as used herein in the context of α-Gal A, means a signal peptide that is not the human α-Gal A signal peptide, typically the signal peptide of some mammalian protein other than α-Gal A.

Skilled artisans will recognize that the human α-Gal A DNA sequence (either cDNA [SEQ ID NO:5] or genomic DNA), or sequences that differ from human α-Gal A DNA due to either silent codon changes or to codon changes that produce conservative amino acid substitutions, can be used to genetically modify cultured human cells so that they will overexpress and secrete the enzyme. Certain mutations in the α-Gal A DNA sequence may encode polypeptides that retain or exhibit improved α-Gal A enzymatic activity. For example, one would expect conservative amino acid substitutions to have little or no effect on the biological activity, particularly if they represent less than 10% of the total number of residues in the protein. Conservative substitutions typically include substitutions within the following groups: glycine, alanine; valine, isoleucine, leucine; aspartic acid, glutamic acid; asparagine, glutamine; serine, threonine; lysine, arginine; and phenylalanine, tyrosine. See, for example, U.S. Pat. No. 5,356,804, incorporated herein by reference.

Fabry Disease

Fabry disease is a genetic disorder caused by deficient activity of the enzyme α-Gal A. By "α-Gal A deficiency," it is meant any deficiency in the amount or activity of this enzyme in a patient, resulting in abnormal accumulations of neutral glycolipids (e.g., globotriaosylceramide) in histiocytes in blood vessel walls, with angiokeratomas on the thighs, buttocks, and genitalia, hypohidrosis, paresthesia in extremities, cornea verticillata, and spoke-like posterior subcapsular cataracts. The deposits of this material can result in pain, serious renal and cardiovascular disease, and stroke. The glycolipid accumulation may induce severe symptoms as typically observed in males who are suffering from Fabry disease. Alternatively, the accumulation may induce relatively mild symptoms, as can sometimes be seen in heterozygous female carriers of the defective gene. Affected individuals have a greatly shortened life expectancy; death usually results from renal, cardiac, or cerebrovascular complications at approximately age 40. There are no specific treatments for this disease. Fabry disease, classified as a lysosomal storage disorder, affects more than 15,000 people world-wide.

Fabry disease as defined above is a complex clinical syndrome characterized by multiorgan and multisystem involvement. Patients who manifest the combination of corneal dystrophy, skin lesions (angiokeratomata), painful neuropathy, cerebral vascular disease, cardiomyopathy, and renal dysfunction are categorized as displaying the "classic" phenotype. There are, however, patients who manifest some, but not all aspects of the classic phenotype. These patients are classified as "atypical variants of Fabry disease." There are several atypical variant phenotypes associated with α-galactosidase A deficiency. For example, some patients with α-galactosidase A deficiency have a variation of Fabry disease with only cardiac involvement, e.g., left ventricular hypertrophy (LVH). There is also another variant phenotype in which patients present with only renal involvement. Although both of these variant phenotypes have been defined in male hemizygotes, the variant forms of Fabry disease have also been described in female heterozygotes as well.

Patients with the atypical cardiac variant generally present with symptomatic disease later in life. The median age of diagnosis for patients with the cardiac variant phenotype is approximately 52 years compared to approximately 29 years for the classic phenotype (Desnick, et al., In *The Metabolic and Molecular Bases of Inherited Disease*, 6th edition (1996). Scriver, et al., (eds), McGraw-Hill (New York). pp. 2741–2784; Meikle, et al., *J. Am. Med. Assoc.* 281: 249–254 (1999)). Patients with this syndrome often present with subtle symptoms of cardiac dysfunction such as exertional dyspnea. Usually, standard echocardiographic analysis reveals that patients with the cardiac variant phenotype are discovered to have left ventricular hypertrophy (LVH) or asymmetric septal hypertrophy. However, patients may also present with myocardial infarction or cardiomyopathy (Scheidt, et al., *New Engl. J. Med.* 324: 395–399 (1991); Nakao, et al., *New Engl. J. Med.* 333: 288–293 (1995)). These patients often undergo myocardial biopsies, and the pathology of the variant syndrome is essentially similar to classic Fabry disease: myocardial infiltration by deposited glycolipid. α-galactosidase A enzyme assays in these patients reveal a broad range of enzyme levels. For example, cardiac variant patients have been reported to have as high as 30% of the normal levels of α-galactosidase A enzyme activity, and, thus, up to now have not been considered as candidates for α-Gal A replacement therapy.

The inventors have now unexpectedly discovered that, although atypical cardiac variant or atypical renal variant patients may have α-galactosidase A enzyme activity levels which are relatively high compared to patients with the classic phenotype of Fabry disease, these patients can also benefit from α-galactosidase A enzyme therapy. For example, patients can have a mutation which produces a kinetically unstable α-Gal A enzyme in the cell, and in these patients α-Gal A enzyme levels can be augmented significantly by administration of α-Gal A preparations of the present invention. Also, some patients with the atypical cardiac variant phenotype have been reported to have a point mutation in amino acid 215 of α-galactosidase A. This amino acid in the unmutated protein is an asparagine which is glycosylated (Eng, et al., *Am. J. Hum. Genet.* 53: 1186–1197. (1993)). Thus, α-Gal A enzyme replacement therapy with a properly glycosylated α-galactosidase A preparations of the present invention can be efficacious in these patients. Furthermore, patients with atypical renal variant have been reported whose only clinical manifestation of Fabry disease is mild proteinuria. Renal biopsy, however, reveals the typical glycolipid inclusions of Fabry disease and α-Gal A enzyme assay reveals lower than normal levels of α-Gal A. However, because deposited ceramide trihexoside in the kidney may be detected in shed renal tubular cells in the urine sediment of these patients, administration of α-Gal A preparations of the present invention can reduce these levels substantially. Lysosomal enzymes such as α-Gal A are targeted to the lysosomal compartment of a cell through interaction with the mannose-6-phosphate (M6P) receptor, which binds to M6P residues present in the oligosaccharide moieties of enzymes destined for the lysosomal compartment. Kornfeld & Mellman, *Ann. Rev. Cell Biol.* 5: 483–525 (1989). The primary interaction occurs in the Golgi, where enzymes bound to Golgi M6P receptors are segregated for transport to the lysosomes. A secondary type of interaction is believed to take place between extracellular α-Gal A and M6P receptors at the cell surface. Enzymes that escape the routing system are secreted by the cell via the constitutive secretory pathway and are often recaptured by cell surface M6P receptors that return the α-galactosidase A to the lysosome by the endocytic pathway. Extracellular substances internalized by cells are transported through the cytoplasm in endocytic vesicles, which fuse with primary lysosomes and empty their contents into the lysosomes. In this process, cell surface M6P receptors are also incorporated into endocytic vesicles and transported to lysosomes. In particular, the α-Gal A preparations of the present invention, in which high levels of sialylation and/or phosphorylation are present, are preferred for the treatment of patients with atypical variants of Fabry disease. Such preparations, for example, minimize the fraction of the injected α-Gal A that is removed by hepatocytes and allow high levels of α-Gal A uptake by non-liver cells, such as renal cells, vascular cells; tubular cells, glomerular cells, cardiac myocytes and cardiac vascular cells.

Extracellular α-Gal A bearing M6P residues may bind to cell surface M6P receptors and be transported into the lysosomal compartment. Once in the lysosomal compartment, α-Gal A can carry out the appropriate function. It is this aspect of lysosomal enzyme trafficking that makes α-galactosidase A enzyme replacement therapy a feasible therapeutic treatment for Fabry disease patients. Thus, even if a cell is genetically deficient in producing α-Gal A, the cell may take up extracellular α-Gal A if the α-Gal A is suitably glycosylated and the deficient cell bears M6P receptors. In patents with Fabry disease, vascular endothelial cells of the kidney and heart display severe histopathologic abnormalities and contribute to the clinical pathology of the disease. These cells, which carry M6P receptors, are a particular therapeutic target of α-Gal A. An object of the invention is to provide an α-Gal A preparation in which M6P is present in the N-linkedoligosaccharides.

The degree to which the N-linked oligosaccharides of α-Gal A are modified by sialylation has a substantial effect on α-Gal A pharmacokinetics and biodistribution. In the absence of appropriate sialylation, α-Gal A is rapidly cleared from the circulation due to binding by hepatic asialoglycoprotein receptors (Ashwell receptors), followed by internalization and degradation by hepatocytes. Ashwell & Harford, *Ann. Rev. Biochem.* 51: 531–554 (1982). This decreases the amount of α-Gal A available in the circulation for binding to M6P receptors on cells which contribute to the clinical pathology of Fabry disease, such as the vascular endothelial cells of the kidney and heart. α-Gal A secreted by genetically-modified human cells has glycosylation properties which are suitable for the treatment of Fabry disease by either conventional pharmaceutical administration of the purified secreted protein or by gene therapy, without requiring additional enzymatic modification as has been reported to be required for the lysosomal enzyme, glucocerebrosidase, in which uptake of purified glucocerebrosidase enzyme by clinically-relevant cells requires complex enzymatic modification of the enzyme following purification from human placenta. Beutler, *New Engl. J. Med.* 325:1354–1360(1991).

Cells Suitable for Production of α-Gal A

An individual suspected of having an α-Gal A deficiency such as Fabry disease can be treated with purified human α-Gal A obtained from cultured, genetically-modified cells, preferably human cells.

When cells are to be genetically modified for the purposes of treatment of Fabry disease, the cells may be modified by conventional genetic engineering methods or by gene activation.

According to conventional methods, a DNA molecule that contains an α-Gal A cDNA or genomic DNA sequence may be contained within an expression construct and transfected into primary, secondary, or immortalized cells by standard methods including, but not limited to, liposome-, polybrene-, or DEAE dextran-mediated transfection, electroporation, calcium phosphate precipitation, microinjection, or velocity driven microprojectiles ("biolistics")(see, e.g., a copending application, U.S. Ser. No. 08/334,797, incorporated herein by reference). Alternatively, one could use a system that delivers the genetic information by viral vector. Viruses known to be useful for gene transfer include adenoviruses, adeno-associated virus, herpes virus, mumps virus, poliovirus, retroviruses, Sindbis virus, and vaccinia virus such as canary pox virus.

Alternatively, the cells may be modified using a gene activation ("GA") approach, such as described in U.S. Pat. Nos. 5,733,761 and 5,750,376, each incorporated herein by reference. α-Gal A made by gene activation is referred to herein as GA-GAL.

Accordingly, the term "genetically modified," as used herein in reference to cells, is meant to encompass cells that express a particular gene product following introduction of a DNA molecule encoding the gene product and/or regulatory elements that control expression of a coding sequence for the gene product. The DNA molecule may be introduced by gene targeting or homologous recombination, i.e., introduction of the DNA molecule at a particular genomic site. Homologous recombination may be used to replace the defective gene itself (the defective α-Gal A gene or a portion of it could be replaced in a Fabry disease patient's own cells with the whole gene or a portion thereof).

As used herein, the term "primary cell" includes cells present in a suspension of cells isolated from a vertebrate tissue source (prior to their being plated, i.e., attached to a tissue culture substrate such as a dish or flask), cells present in an explant derived from tissue, both of the previous types of cells plated for the first time, and cell suspensions derived from these plated cells.

"Secondary cells" refers to cells at all subsequent steps in culturing. That is, the first time a plated primary cell is removed from the culture substrate and replated (passaged), it is referred to as a secondary cell, as are all cells in subsequent passages.

A "cell strain" consists of secondary cells which have been passaged one or more times; exhibit a finite number of mean population doublings in culture; exhibit the properties of contact-inhibited, anchorage dependent growth (except for cells propagated in suspension culture); and are not immortalized.

By "immortalized cell" is meant a cell from an established cell line that exhibits an apparently unlimited lifespan in culture.

Examples of primary or secondary cells include fibroblasts, epithelial cells including mammary and intestinal epithelial cells, endothelial cells, formed elements of the blood including lymphocytes and bone marrow cells, glial cells, hepatocytes, keratinocytes, muscle cells, neural cells, or the precursors of these cell types. Examples of immortalized human cell lines useful in the present methods include, but are not limited to, Bowes Melanoma cells (ATCC Accession No. CRL 9607), Daudi cells (ATCC Accession No. CCL 213), HeLa cells and derivatives of HeLa cells (ATCC Accession Nos. CCL 2, CCL 2.1, and CCL 2.2), HL-60 cells (ATCC Accession No. CCL 240), HT-1080 cells (ATCC Accession No. CCL 121), Jurkat cells (ATCC Accession No. TIB 152), KB carcinoma cells (ATCC Accession No. CCL 17), K-562 leukemia cells (ATCC Accession No. CCL 243), MCF-7 breast cancer cells (ATCC Accession No. BTH 22), MOLT-4 cells (ATCC Accession No. 1582), Namalwa cells (ATCC Accession No. CRL 1432), Raji cells (ATCC Accession No. CCL 86), RPMI 8226 cells (ATCC Accession No. CCL 155), U-937 cells (ATCC Accession No. CRL 1593), WI-38VA13 sub line 2R4 cells (ATCC Accession No. CLL 75.1), CCRF-CEM cells (ATCC Accession No. CCL 119), and 2780AD ovarian carcinoma cells (Van der Blick et al., *Cancer Res.* 48: 5927–5932, 1988), as well as heterohybridoma cells produced by fusion of human cells and cells of another species.

Following the genetic modification of human cells to produce a cell which secretes α-Gal A, a clonal cell strain consisting essentially of a plurality of genetically identical cultured primary human cells or, where the cells are immortalized, a clonal cell line consisting essentially of a plurality of genetically identical immortalized human cells, may be generated. In one embodiment, the cells of the clonal cell strain or clonal cell line are fibroblasts. In a preferred embodiment the cells are secondary human fibroblasts, e.g., BRS-11 cells.

After genetic modification, the cells are cultured under conditions permitting secretion of α-Gal A. The protein is isolated from the cultured cells by collecting the medium in which the cells are grown, and/or lysing the cells to release their contents, and then applying protein purification techniques.

Purification of α-Gal A from the Conditioned Medium of Stably Transfected Cells

According to the methods of this invention, the α-Gal A protein is isolated from the cultured cells ("α-Gal A production cells") by collecting the medium in which the cells are grown, or lysing the cells to release their contents, and then applying protein purification techniques without the use of lectin affinity chromatography. The preferred purification process is outlined in Example 2 below.

Alternative hydrophobic interaction resins, such as Source Iso (Pharmacia), Macro-Prep® Methyl Support (Bio-Rad), TSK Butyl (Tosohaas) or Phenyl Sepharose® (Pharmacia), can also be used to purify α-Gal A. The column can be equilibrated in a relatively high concentration of a salt, e.g., –1_M ammonium sulfate or 2 M sodium chloride, in a buffer of pH 5.6. The sample to be purified is prepared by adjusting the pH and salt concentration to those of the equilibration buffer. The sample is applied to the column and the column is washed with equilibration buffer to remove unbound material. The α-Gal A is eluted from the column with a lower ionic strength buffer, water, or organic solvent in water, e.g., 20% ethanol or 50% propylene glycol. Alternatively, the .Gal A can be made to flow through the column by using a lower concentration of salt in the equilibration buffer and in the sample or by using a different pH. Other proteins may bind to the column, resulting in purification of the α-Gal A-containing sample which did not bind the column. A preferred first purification step is the use of a hydroxyapatite column.

An alternative step of purification can use a cation exchange resin, e.g., SP Sepharose(® 6 Fast Flow (Pharmacia), Source 30S (Pharmacia), CM Sepharose® Fast Flow (Pharmacia), Macro-Prep® CM Support (Bio-Rad) or Macro-Prep® High S Support (Bio-Rad), to purify α-Gal A. The "first chromatography step" is the first application of a sample to a chromatography column (all steps associated with the preparation of the sample are excluded). The α-Gal A can bind to the column at pH 4.4. A buffer, such as 10 mM sodium acetate, pH 4.4, 10 mM sodium citrate, pH 4.4, or other buffer with adequate buffering capacity at approximately pH 4.4, can be used to equilibrate the column. The sample to be purified is adjusted to the pH and ionic strength of the equilibration buffer. The sample is applied to the column and the column is washed after the load to remove unbound material. A salt, such as sodium chloride or potassium chloride, can be used to elute the axial A from the column. Alternatively, the α-Gal A can be eluted from the column with a buffer of higher pH or a combination of higher salt concentration and higher pH. The α-Gal A can also be made to flow through the column during loading by increasing the salt concentration in the equilibration buffer and in the sample load, by running the column at a higher pH, or by a combination of both increased salt and higher pH.

Another step of purification can use a Q Sephrarose® 6 Fast Flow for the purification of α-Gal A. Q Sephrarose® 6 Fast Flow is a relatively strong anion exchange resin. A weaker anion exchange resin such as DEAE Sepharose® Fast Flow (Pharmacia) or Macro-Prepg DEAB (Bio-Rad) can also be used to purify α-Gal A. The column is equilibrated in a buffer, e.g., 10 mM sodium phosphate, pH 6. The pH of the sample is adjusted to pH 6, and low ionic strength is obtained by dilution or diafiltration of the sample. The sample is applied to the column under conditions that bind α-Gal A. The column is washed with equilibration buffer to remove unbound material. The α-Gal A is eluted with application of salt, e.g., sodium chloride or potassium chloride, or application of a lower pH buffer, or a combination of increased salt and lower pH. The α-Gal A can also be made to flow through the column during loading by increasing the salt concentration in the load or by running the column at a lower pH, or by a combination of both increased salt and lower pH.

Another step of purification can use a Superdex® 200 (Pharmacia) size exclusion chromatography for purification of α-Gal A. Other size exclusion chromatography resins such as Sephacryl® S-200 HR or Bio-Gel® A-1.5 m can also be used to purify α-Gal A. The preferred buffer for size exclusion chromatography is 25 mM sodium phosphate, pH 6.0, containing 0.15 M sodium chloride. Other formulation-compatible buffers can also be used, e.g., 10 mM sodium or potassium citrate. The pH of the buffer can be between pH 5 and pH 7 and should at contain a salt, e.g., sodium chloride or a mixture of sodium chloride and potassium chloride.

Another step of purification can use a chromatofocusing resin such as Polybuffer Exchanger PBE 94 (Pharmacia) to purify α-Gal A. The column is equilibrated at relatively high pH (e.g., pH 7 or above), the pH of the sample to be purified is adjusted to the same pH, and the sample is applied to the column. Proteins are eluted with a decreasing pH gradient to a pH such as pH 4, using a buffer system, e.g., Polybuffer 74 (Pharmacia), which had been adjusted to pH4.

Alternatively, immunoaffinity chromatography can be used to purify α-Gal A. An appropriate polyclonal or monoclonal antibody to α-Gal A (generated by immunization with α-Gal A or with a peptide derived from the α-Gal A sequence using standard techniques) can be immobilized on an activated coupling resin, e.g., NHS-activated Sepharose® 4 Fast Flow (Pharmacia) or CNBr-activated Sepharose® 4 Fast Flow (Pharmacia). The sample to be purified can be applied to the immobilized antibody column at about pH 6 or pH 7. The column is washed to remove unbound material. α-Gal A is eluted from the column with typical reagents utilized for affinity column elution such as low pH, e.g., pH 3, denaturant, e.g., guanidine HCl or thiocyanate, or organic solvent, e.g., 50% propylene glycol in a pH 6 buffer. The purification procedure can also use a metal chelate affinity resin, e.g., Chelating Sepharose® Fast Flow (Pharmacia), to purify α-Gal A. The column is pre-charged with metal ions, e.g., $Cu^{2+}$, $Zn^{2+}$, $Ca^{2+}$, $Mg^{2+}$ or $Cd^{2+}$. The sample to be purified is applied to the column at an appropriate pH, e.g., pH 6 to 7.5, and the column is washed to remove unbound proteins. The bound proteins are eluted by competitive elution with imidazole or histidine or by lowering the pH using sodium citrate or sodium acetate to a pH less than 6, or by introducing chelating agents, such as EDTA or EGTA.

According to the foregoing protocols, this invention provides preparations with a higher purity α-Gal A preparation than prepared in the prior art, purified to at least 98% homogeneity, more preferably to at least 99% homogeneity, and most preferably to at least 99.5% homogeneity, as measured by SDS-PAGE or reverse phase HPLC. The α-Gal A preparations of the present invention may comprise numerous α-Gal A glycoforms. Accordingly, the term "homogeneity," as used herein in the context of α-Gal A preparations, refers to preparations that are substantially free (<2% of the total proteins) of proteins other than α-Gal A. Examples of non-α-Gal A proteins such as albumin, non-α-Gal A proteins produced by the host cell, and non-α-Gal A proteins isolated from animal tissue or fluid. The specific activity of the α-Gal A preparations of the present invention is preferably at least $2.0 \times 10^6$ units/mg protein, more preferably at least $3.0 \times 10^6$ units/mg protein, and most preferably at least $3.5 \times 10^6$ units/mg protein.

Improving Circulating Half-Life of α-Gal A Preparations by Glycan Remodeling to Increase Oligosaccharide Charge The invention provides a glycoprotein modification program for increased uptake of a therapeutic enzyme in specific tissues other than liver and macrophages. Using the methods of the present invention, human glycosylated α-Gal A preparations are obtained, wherein between 35% and 85% of the oligosaccharides are charged, preferably at least 50% of the oligosaccharides being charged.

Protein N-glycosylation functions by modifying appropriate asparagine residues of proteins with oligosaccharide structures, thus influencing their properties and bioactivities. Kukuruzinska & Lennon, Crit. Rev. Oral. Biol. Med. 9: 415–48 (1998). The present invention provides an isolated α-Gal A preparation in which a high percentage of the oligosaccharides are negatively charged, primarily by the addition of one to four sialic acid residues on complex glycans, or of one to two phosphate moieties on high-mannose glycans, or of a single phosphate and a single sialic acid on hybrid glycans. Smaller amounts of sulfated complex glycans may also be present. A high proportion of charged structures serves two main functions. First, capping of penultimate galactose residues by 2,3- or 2,6-linked sialic acid prevents premature removal from the circulation by the asialoglycoprotein receptor present on hepatocytes. This receptor recognizes glycoproteins with terminal galactose residues. Increasing the circulatory half-life of α-Gal A gives important target organs such as heart and kidney the opportunity to endocytose greater amounts of enzyme from the plasma following enzyme infusion. Second, the presence of Man-6-phosphate on high-mannose or hybrid glycans provides an opportunity for receptor-mediated uptake by the cation-independent Man-6-phosphate receptor (CI-MPR). This receptor-mediated uptake occurs on the surface of many cells, including vascular endothelial cells, which are a major storage site of CTH in Fabry patients. Enzyme molecules with two Man-6-phosphate residues have a much greater affinity for the CI-MPR than those with a single Man-6-phosphate. Representative glycan structures are provided in Table 1.

TABLE 1

Representative Glycan Structures

A biantennary glycan:

```
                          ±Fucα1,6
SAα2,3/6Galβ1,4GlcNAcβ1,2Manα1,6         |
                              \
                               Manβ1,4GlcNAcβ1,4GlcNac-Asn
SAα2,3/6Galβ1,4GlcNAcβ1,2Manα1,3/
```

A tetraantennary glycan:

```
SAα2,3/6Galβ1,4GlcNAcβ1,6
                        \
                                             ±Fucα1,6
    SAα2,3/6Galβ1,4GlcNAcβ1,2Manα1,6            |
                                    \
                                     ManI3 1,4GlcNAcf3l,4GlcNac-Asn
    SAα2,3/6Galβ1,4GlcNAcβ1,2Manα1,3/
                                /
SAα2,3/6Galβ1,4GlcNAcβ1,4
```

A high-mannose glycan:

TABLE 1-continued

Representative Glycan Structures

```
Manα1,2Manα1,6
              \
               Manα1,6
              /        \
Manα1,2Manα1,3           Manβ1,4GlcNAcβ1,4GlcNac-Asn
                        /
Manα1,2Manα1,2Manα1,3
```

A phosphorylated hybrid glycan:

```
P-Manα1,6
         \
          Manα1,6
         /        \
   Manα1,3         Manβ1,4GlcNAcβ1,4GlcNac-Asn
                  /
SAα2,3/6Galβ1,4GlcNAcβ1,2Manα1,3
```

A bisphosphorylated glycan:

TABLE 1-continued

Representative Glycan Structures

```
P-Manα1,2Manα1,6
                \
                 Manα1,6
                /        \
         Manα1,3          Manβ1,4GlcNAcβ1,4GlcNac-Asn
                         /
         P-Manα1,2Manα1,3
```

N-glycoprotein biosynthesis involves a multitude of enzymes, glycosyltransferases, and glycosidases. The majority of these enzymes function in the endoplasmic reticulum(ER) and Golgi apparatus in an ordered and well-orchestrated manner. The complexity of N-glycosylation is augmented by the fact that different asparagine residues within the same polypeptide may be modified with different oligosaccharide structures, and various proteins are distinguished from one another by the characteristics of their carbohydrate moieties. Recent advances in molecular genetics have expedited the identification, isolation, and characterization of N-glycosylation genes. As a result, information regarding relationships between N-glycosylation and other cellular functions has emerged.

N-linked glycoprotein processing in the cell begins when an oligosaccharide chain with a $Glc_3Man_9GlcNAc_2$ is added to an acceptor asparagine on a nascent peptide in the lumen of the ER as a single unit. A fourteen sugar oligosaccharide chain consisting of $Glc_3Man_9GlcNAc_2$ is built up on dolichol, a very long chain aliphatic alcohol:

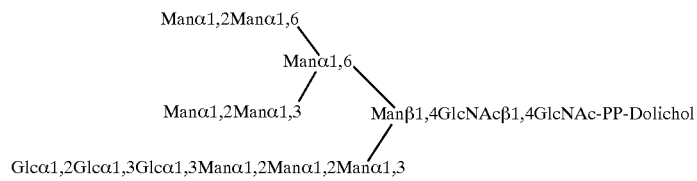

This oligosaccharide is transferred as a single unit to an acceptor asparagine residue on a nascent peptide chain in the lumen of the ER. The large size of the glycan relative to the peptide may guide protein folding. The three glucose residues serve as a signal that the oligosaccharide is completed and ready for transfer by oligosaccharyl transferase. This enzyme will also transfer nonglucosylated oligosaccharides but at only a fraction of the rate of the completed chain because these are sub-optimal substrates. One form of carbohydrate deficient glycoprotein syndrome in humans has been shown to be caused by a deficiency of Dolichol-P-Glc: $Man_9GlcNAc_2$-PP-Dolichol glucosyl transferase, the first enzyme in the glucose addition pathway, which results in hypoglycosylation of serum proteins. Korner et al., *Proc. Natl. Acad. Sci. USA* 95: 13200–13205 (1998). After removal of the three glucose residues and achievement of the correct conformation, the newly synthesized glycoprotein is exported to the Golgi. Depending on the accessibility of the glycan to Golgi mannosidases after protein folding, the glycan chain may stay as a high mannose chain with 5–9 mannose residues. Alternatively, the glycan chain may be further processed to a trimannosyl core, and become an acceptor for other glycosyl transferases that form complex chains by addition of more GlcNAc residues, followed by Gal, NeuAc and Fuc. A third possibility, if the protein has two lysine residues exactly 34 angstroms apart and in the correct spatial relationship to a high mannose chain, is the addition of GlcNAcα-1-PO$_4$ onto carbon 6 of one, or sometimes two, mannose residues. Cuozzo et al., *J. Biol. Chem.* 273: 21069–21076 (1998). After removal of the α-linked GlcNAc by a specific enzyme, a terminal M6P epitope is generated which is recognized by a M6P receptor in the trans Golgi network that then targets these enzymes to lysosomes in cells of mesenchymal origin.

To target α-Gal A to as many different tissues as possible, many different carbohydrate structures (glycoforms) are useful. Matsuura et al., *Glycobiology* 8: 329–339 (1998) reported that the glycan structures on human α-Gal A made in CHO cells had 41% high-mannose glycans and the phosphorylation level was 24%. However, the level of sialylated complex glycans was only 11%. Thus, ⅔ of the complex chains were not sialylated, which results in the rapid elimination of α-Gal A by the liver. The α-Gal A produced in the human cells of the invention has a higher percentage of charged oligosaccharides than the prior art α-Gal A produced in CHO cells. For example, α-Gal A synthesized in HT-1080 cells described herein is particularly suitable, because α-Gal A produced in HT-1080 cells contains approximately 15% neutral structures (high-mannose and hybrid), approximately 16% phosphorylated glycans, and approximately 67% complex glycans with 2 to 4 sialic acid residues. Thus, essentialy all of the complex chains are sialylated as compared to α-Gal A produced in CHO cells. HT-1080 cell α-Gal A has three N-linked glycosylation sites. Two sites are processed to complex glycans in the Golgi apparatus, while the third site is occupied by a high-mannose glycan, 50% of which is modified by lysosomal enzyme-specific phosphorylation to yield both monophosphorylated and diphosphorylated species.

Four approaches are provided for carbohydrate remodeling on a protein containing N-linked glycan chains. First, the proportion of charged α-Gal A can be increased by selective isolation of glycoforms during the purification process. The present invention provides for increasing the proportion of highly charged and higher molecular weight α-Gal A glycoforms by fractionation of α-Gal A species on chromatography column resins during and/or after the purification process. The more highly charged glycoform species of α-Gal A contain more sialic acid and/or more phosphate, and the higher molecular weight glycoforms would also contain the fully glycosylated, most highly branched and highly charged species. Selection of the charged species, or removal of the non-glycosylated, poorly glycosylated or poorly sialylated and/or phosphorylated α-Gal A species would result in a population of α-Gal A glycoforms with more sialic acid and/or more phosphate, therefore providing an α-Gal A preparation with higher half-life and potential therapeutic efficiency.

This fractionation process can occur on, but is not limited to, suitable chromatographic column resins utilized to purify or isolate α-Gal A. For example, fractionation can occur on, but is not limited to, cation exchange resins (such as SP-Sepharose®), anion exchange resins (Q-Sepharose®), affinity resins (Heparin Sepharose®, lectin columns) size exclusion columns (Superdex® 200) and hydrophobic interaction columns (Butyl Sepharose®) and other chromatographic column resins known in the art.

Since α-Gal A is produced in cells as a heterogeneous mixture of glycoforms which differ in molecular weight and charge, α-Gal A tends to elute in relatively broad peaks from the chromatography resins. Within these elutions, the glycoforms are distributed in a particular manner depending on the nature of the resin being utilized. For example, on size exclusion chromatography, the largest glycoforms will tend to elute earlier on the elution profile than the smaller glycoforms.

On ion exchange chromatography, the most negatively charged glycoforms will tend to bind to a positively charged resin (such as Q-Sepharose® with higher affinity than the less negatively charged glycoforms, and will therefore tend to elute later in the elution profile. In contrast, these highly negatively charged glycoforms may bind less tightly to a negatively charged resin, such as SP Sepharose®, than less negatively charges species, or may not even bind at all.

Fractionation of the glycoform species on chromatographic resins can be influenced by pH, ionic strength, buffer salt selection, viscosity and/or other parameters such choice of resin type. The use of various types of gradient elutions (straight line linear gradients, curved, e.g., exponential gradients) or use of a series of short step elutions to selectively elute α-Gal A species from the chromatography column can also be optimized for α-Gal A fractionation. All of these factors, alone or in combination, can be optimized to achieve efficient fractionation of the glycoforms. Fractionation can also occur after the purification process is completed, on a particular chromatographic resin selectively optimized for the fractionation and selection of the desired glycoform population.

Selection of glycoform populations from the fractionated α-Gal A species can be achieved after analysis of the eluted α-Gal A glycoforms. The elution peak can be analyzed by various techniques such as, but not limited to, SDS-PAGE, isoelectric focusing, capillary electrophoresis, analytical ion exchange HPLC, and/or analytical size exclusion HPLC. Particular fractions can be selected which tend towards the desired size or charge profile. Selection can occur at every chromatographic step in the process, allowing for gradual achievement of the desired glycoform population, or can be limited to a particular step or steps if the efficiency of fractionation of the step(s) is high. Fractionation can also occur after the purification process is completed, on a particular chromatographic resin selectively optimized for the fractionation and selection of the desired glycoform population.

Fractionation and selection of highly charged and/or higher molecular weight glycoforms of α-Gal A can be performed on any α-Gal A preparation, such as that derived from genetically modified cells such as cells modified by conventional genetic engineering methods or by gene activation (GA). It can be performed on cell lines grown in optimized systems to provide higher sialylation and phosphorylation as described above, or PEGylated α-Gal A as described below.

For example, in the α-Gal A purification process as described herein, fractionation of α-Gal A glycoforms can occur at various steps in the process. On the hydrophobic resin, Butyl Sepharose® Fast Flow, the highest charged α-Gal A glycoforms elute first, followed by the less highly charges species. For Heparin Sepharose®, the highest charged species also elute first in the elution peak, followed by the less highly charged species. The opposite occurs with Q-Sepharose®, where the least highly charged species eluting first, followed by the most highly charged glycoforms. On size exclusion chromatography on Superdex® 200, the highest molecular weight glycoforms elute first followed by the lower molecular weight, less glycosylated α-Gal A species. To allow for efficient fractionation of particular α-Gal A glycoform populations, multiple chromatographic steps can be combined, all of which fractionate on different physical methods. For example, to obtain the α-Gal A glycoforms containing the lowest pI (those containing the most negative charge) limiting the pooling the early eluting butyl fractions would enhance for the more highly charged α-Gal A. Proceeding with this selected pool on the Heparin column, and again limiting the pooling to the earlier, more highly negatively charged α-Gal A species further enhances the proportion of low pI α-Gal A glycoforms in the pool. Further fine tuning of the glycoform population can be done at various steps of the purification process by monitoring the size and charge distribution of the elution pools by SDS-PAGE and isoelectric focusing. An example of fractionation by size and charge is outlined below in Example 2.4.

The second approach for carbohydrate remodeling involves modifying certain glycoforms on the purified α-Gal A by attachment of an additional terminal sugar residue using a purified glycosyl transferase and the appropriate nucleotide sugar donor. This treatment affects only those glycoforms that have an appropriate free terminal sugar residue to act as an acceptor for the glycosyl transferase being used. For example, α2,6-sialyl transferase adds sialic acid in an a 2,6-linkage onto a terminal Galβ1,4GlcNAc-R acceptor, using CMP-sialic acid as the nucleotide sugar donor. Commercially available enzymes and their species of origin include: fucose α1,3 transferases III, V and VI (humans); galactose α1,3 transferase (porcine); galactose β1,4 transferase (bovine); mannose α1,2 transferase (yeast); sialic acid α2,3 transferase (rat); and sialic acid α2,6 transferase (rat). After the reaction is completed, the glycosyl transferase can be removed from the reaction mixture by a glycosyl transferase specific affinity column consisting of the appropriate nucleotide bonded to a gel through a 6 carbon spacer by a pyrophosphate (GDP, UDP) or phosphate (CMP) linkage or by other chromatographic methods known in the art. Of the glycosyl transferases listed above, the sialyl transferases is particularly useful for modification of enzymes, such as α-Gal A, for enzyme replacement therapy in human patients. Use of either sialyl transferase with CMP-5-fluoresceinyl-neuraminic acid as the nucleotide sugar donor yields a fluorescently labeled glycoprotein whose uptake and tissue localization can be readily monitored.

The third approach for carbohydrate remodeling involves glyco-engineering, e.g., introduction of genes that affect glycosylation mechanisms of the cell, of the α-Gal A production cell to modify post-translational processing in the Golgi apparatus is a preferred approach.

The fourth approach for carbohydrate remodeling involves treating α-Gal A with appropriate glycosidases to reduce the number of different glycoforms present. For example, sequential treatment of complex glycan chains with neuraminidase, β-galactosidase, and β-hexosaminidase cleaves the oligosaccharide to the trimannose core.

The structure of an N-linked glycan depends on the accessibility of the glycan chain to Golgi processing mannosidases after the protein has folded, and the presence in the Golgi of a family of glycosyl transferases and the appropriate nucleotide sugar donors. Many of the glycosyl transferases catalyze competing reactions, which can result in the glycan chain being elongated in several different and compatible ways, depending on which enzyme reacts first. This results in microheterogeneity and the formation of a complex family of glycoforms. Some structures are unique to a single tissue, such as the modification of certain pituitary hormones by the addition of GalNAc-4-SO$_4$, or are limited to a few organs.

An example of the latter is the formation of a so-called bisecting GlcNAc (GlcNAc linked β1,4 to the core β-mannose residue) on complex glycans of glutamyl-transpeptidase in kidney, but not in liver. A bisected biantennary structure on γ-glutamyltranspeptidase is shown below:

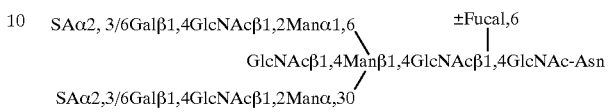

In mammals, the enzyme responsible, GlcNAc transferase III (GnT-III), is found in certain cells of the brain and kidney and in certain cells of the liver in patients with hepatocarcinomas. GnT-III catalyzes the addition of N-acetylglucosamine in β 1–4 linkage to the β-linked mannose of the trimannosyl core of N-linked sugar chains to produce a bisecting GlcNAc residue. The mouse, rat, and human genes for GnT-III have been cloned. Ihara et al., *J. Biochem.* (*Tokyo*) 113: 692–698 (1993).

The presence of additional GlcNAc T-III activity in human cells can produce an increase in monophosphorylated hybrid glycans at the expense of bi-, tri-, and tetrantennary complex glycans. This should not affect the plasma half-life adversely, but may increase targeting to vascular endothelial cells. A representative structure is shown below:

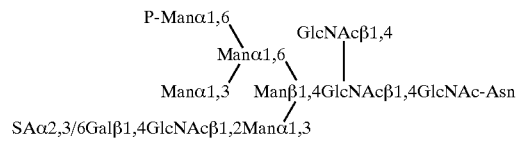

Some of the α-Gal A is taken up by the kidney and results in a significant decrease in the stored glycolipids. Because the kidney can form N-glycans with bisecting GlcNAc residues, renal epithelial cells can recognize glycoproteins with this epitope with a particularly high specificity.

Elevated GnT-III activity cancause an imbalance in branching on the trimannosyl core by inhibiting further branching by GnT-II, IV, V, and Gal β1,4-transferase at the substrate level. Recently, a Chinese hamster ovary (CHO) cell line capable of producing bisected oligosaccharides on glycoproteins was created by overexpression of recombinant GnT-III. Sburlati et al., *Biotechnol. Progr.* 14: 189–192 (1998). Interferon β (IFN-β) was chosen as a model and potential therapeutic secreted heterologous protein on which the effect of GnT-III-expression on product glycosylation could be evaluated. IFN-β with bisected oligosaccharides was produced by the GnT-III-engineered CHO cells, but not by the unmodified parental cell line.

The production of glycoprotein therapeutics requires characterization of glycosylation with respect to the lot-to-lot consistency. The 'hypothetical N-glycan charge Z' has been used as a parameter to characterize the protein glycosylation in a simple, efficient manner. The determination of Z has been validated in multiple repetitive experiments and proved to be highly accurate and reliable. Hermentin et al., *Glycobiology* 6: 217–230 (1996). The hypothetical N-glycan charge of a given glycoprotein is deduced from the N-glycan mapping profile obtained via high performance anion-exchange chromatography (HPAEC)/pulsed amperometric detection (PAD). In HPAEC, N-glycans are clearly separated according to their charge, e.g., their number of sialic acid residues, providing distinct regions for neutral structures as well as for the mono- di-, tri-, and tetrasialylated N-glycans. Z is defined as the sum of the products of the respective areas (A) in the asialo, monosialo, disialo, trisialo, tetrasialo, and pentasialo region, each multiplied by the corresponding charge:

$$Z=A_{(asialo)}\cdot+A_{(MS)}\cdot 1+A_{(DiS)}\cdot 2+A_{(TriS)}\cdot 3+A_{(TetraS)}\cdot 4[+A_{(pentaS)}\cdot 5]Z= \Sigma A_{(i)}\cdot (i)$$

where i is 0 in the asialo region, 1 in the monosialo (MS) region, 2 in the disialo (DiS) region, 3 in the trisialo (TriS) region, 4 in the tetrasialo (TetraS) region, and 5 in the pentasialo (PentaS)region.

Thus, a glycoprotein with mostly C4-4* structures will provide $Z \cong 400$, a glycoprotein carrying largely C2-2* structures will amount to $Z \cong 200$, and a glycoprotein carrying only high-mannose type or truncated structures will provide $Z \cong 0$.

Human glycosylated α-Gal A preparations of the present invention have an oligosaccharide charge, as measured by the Z number, greater than 100, preferably greater than 150, and more preferably greater than 170.

Altering the Half-Life of Serum α-Gal A by Phosphorylation

Phosphorylation of α-Gal A may be altered to affect the circulating half-life of α-Gal A and the level of α-Gal A entering cells. The phosphorylation is preferably achieved within the cell expressing α-Gal A. Specifically contemplated is obtaining a glycosylated α-Gal A preparation with increased phosphorylation by first introducing into an α-Gal A producing-cell a DNA sequence which encodes for phosphoryl transferase, or by introducing a regulatory sequence by homologous recombination that regulates expression of an endogenous phosphoryl transferase gene. The α-Gal A production cell is then cultured under culture conditions which result in expression of α-Gal A and phosphoryl transferase. Isolation can then be performed of the α-Gal A preparation with increased phosphorylation compared to the α-Gal A produced in a cell without the polynucleotide. Such phosphoryl transferases are well known in the art. See, for example, U.S. Pat. Nos. 5,804,413 and 5,789,247, each incorporated herein by reference.

The concerted actions of two membrane-bound Golgi enzymes are needed to generate a Man-6-phosphate recognition marker on a lysosomal proenzyme. The first, UDP-N-acetylglucosamine: glycoprotein N-acetylglucosamine-1-phosphotransferase (GlcNAc phosphotransferase), requires a protein recognition determinant on lysosomal enzymes that consists of two lysine residues exactly 34 Å apart and in the correct spatial relationship to a high mannose chain. The second, N-acetylglucosamine-1-phosphodiestera-N-acetylglucosaminidase (phosphodiester a-GlcNAcase), hydrolyzes the α-GlcNAc-phosphate bond exposing the Man-6-phosphate recognition site.

According to the methods of this invention, the α-Gal A preparations produced by the methods of the present invention have multiple glycoforms with between 16–50%, preferably 25–50%, more preferably at least 30%, of glycoforms being phosphorylated.

Altering the Half-Life of Serum α-Gal A by Increased Sialylation

Increased sialylation of undersialylated glycans with terminal galactose residues can be accomplished by transfection of mammalian and preferably human cells with sialyl transferase gene.

The present invention provides a glycosylated α-Gal A preparation having an increased oligosaccharide charge produced by first introducing a polynucleotide, which encodes for sialyl transferase, into an α-Gal A producing-cell, or introducing a regulatory sequence by homologous recombination that regulates expression of an endogenous sialyl transferase gene. The α-Gal A production cell is then cultured under culture conditions which result in expression of α-Gal A and sialyl transferase. The following step consists of isolating the α-Gal A preparation with increased oligosaccharide charge. Preferred sialyl transferases include an α2,3-sialyl transferase and an α2,6-sialyl transferase. These sialyl transferases are well known. For example, see U.S. Pat. No. 5,858,751, incorporated herein by reference.

In a preferred embodiment, this method of increasing sialylation includes the additional step of selecting for α-Gal A glycoforms with increased size or increased charge by fractionation or purification of the preparation (as discussed below).

Alternatively, the invention provides for increasing sialylation by maintaining cells in a low ammonium environment. In particular, a glycosylated α-Gal A preparation with increased sialylation is obtained by contacting an α-Gal A production cell with a culture medium having an ammonium concentration below 10 mM, more preferably below 2 mM. Increased sialylation can be accomplished by perfusion of production cells by which toxic metabolites, such as ammonia, are periodically removed from the culture medium. In a preferred embodiment, the low ammonium environment is achieved by addition of the glutamine synthetase gene or cDNA to the production cells. Alternatively, the low ammonium environment is achieved by perfusion of the α-Gal A production cell with fresh culture medium to maintain the ammonium concentration below 10 mM, more preferably below 2 mM. The production cells may be perfused continuously with fresh culture medium with an ammonium concentration below 10 mM, more preferably below 2 mM. Alternatively, the production cells may be perfused intermittently with fresh culture medium. Intermittent perfusion, as used herein, refers to either perfusion at regular, periodic intervals of time, or after a measurement of the ammonium concentration approaching the target concentration (ie., 10 mM, more preferably below 2 mM). The intermittent perfusions should be at intervals sufficiently frequent such that the ammonium concentration never exceeds the target concentration. The production cells are perfused for a period of time necessary to obtain an α-Gal A preparation with between 50–70%, preferably 60%, of the total glycans being sialylated.

Increasing Circulating Half-Life of Serum α-Gal A By PEGylation of α-Gal A

Also according to this invention, the circulatory half-life of a human glycosylated α-Gal A preparation is enhanced by complexing α-Gal A with polyethylene glycol. Poly (ethylene glycol) (PEG) is a water soluble polymer that when covalently linked to proteins, alters their properties in ways that extend their potential uses. Polyethylene glycol modification ("PEGylation") is a well established technique which has the capacity to solve or ameliorate many of the problems of protein and peptide pharmaceuticals.

The improved pharmacological performance of PEG-proteins when compared with their unmodified counterparts prompted the development of this type of conjugate as a therapeutic agent. Enzyme deficiencies for which therapy with the native enzyme was inefficient (due to rapid clearance and/or immunological reactions) can now be treated with equivalent PEG-enzymes. For example, PEG-adenosine deaminase has already obtained FDA approval. Delgado et al., *Crit. Rev. Ther. Drug Carrier Syst.* 9: 249–304 (1992).

The covalent attachment of PEG to α-galactosidase from green coffee beans alters the catalytic properties of the enzyme by masking specific determinant sites on the molecule. This results in an increase in $K_m$ and a decrease in $V_{max}$ values against p-nitrophenyl substrate analogs. Wieder & Davis, *J. Appl. Biochem.* 5: 337–47 (1983). α-galactosidase was still able to cleave terminal galactose residues from human saliva blood group substance B. Antibody and lectin-specific binding were lost from PEG-α-galactosidase. Antibodies generated from native α-galactosidase can block enzyme activity, and this inhibition is gradually lost when tested against preparations of the enzyme with progressively higher amounts of PEG. By contrast, antisera from animals immunized with PEG-α-galactosidase did not inhibit enzyme activity in any α-galactosidase or PEG-α-galactosidase preparation. These results indicate that PEG tends to cover lectin-specific carbohydrate moieties and antigenic determinants and that these sites probably remain cryptic during in vivo processing of PEG-enzymes.

Covalent attachment of PEG to proteins requires activation of the hydroxyl terminal group of the polymer with a suitable leaving group that can be displaced by nucleophilic attack of the ε-amino terminal of lysine and the α-amino group of the N-terminus. Several chemical groups have been exploited to activate PEG. For each particular application, different coupling methods provide distinct advantages. Different methods of PEGylation have a surprising and dramatic impact on factors such as retention of bioactivity, stability and immunogenicity of the resulting PEGylated proteins and peptides. Francis et al., *Int. J. Hematol.* 68(1): 1–18 (1998). For example, a linkerless PEGylation technique attaches only PEG to the target molecule. More specifically, the application of a biologically optimized PEGylation technique, using tresyl monomethoxy PEG (TMPEG), to a variety of target proteins reveals, as described by Francis et al., *Int. J. Hematol.* 68(1): 1–18 (1998), an exceptional ability to conserve biological activity of the target. This, and the benefit of adding nothing other than PEG (which has been shown to be safe for use in human therapeutics), to the protein makes the method ideal for the modification of α-Gal A.

Four possible sites for coupling PEG to proteins are the (1) amino groups (N-terminus and lysine); (2) carboxyl groups (aspartic acid and glutamic acid); (3) sulfhydryl groups (cysteine); and (4) carbohydrate groups (aldehydes generated after periodate treatment). Coupling to the carboxyl groups of proteins and to aldehyde groups on carbohydrates requires a PEG reagent with a nucleophilic amino group. This chemistry changes the pI of α-Gal A after the negatively charged carboxyl groups are bound by PEG. Any changes in pI may affect the biological activity of α-Gal A. Furthermore, coupling PEG to the carbohydrate chains may affect uptake of α-Gal A by the M6P receptor, which is critical for biological activity. Sulfhydryl chemistry also affects the physical structure of the molecule and is not recommended.

Commonly used methods for PEGylation form an amide bond between the amino groups of a protein and the methoxy group on monomethoxy-PEG. NHS-PEG is commercially available and results in an amide bond between the protein and PEG. However amide bond formation changes pI due to the loss of the positive charge of the —$NH_2$ group.

A method for coupling PEG to α-Gal A without affecting its pI uses tresyl-PEG. Tresyl-PEG couples through amino groups and form a stable secondary amine. Secondary amines offer the advantage of retaining the positive charge of the amino group. The tresyl-PEG reagent is commercially available and is stable as a lyophilized and desiccated powder. Tresyl-PEG has been thoroughly characterized and the reaction and by-products are well understood. Accordingly, in a preferred embodiment, the α-Gal A preparation is complexed using tresyl monomethoxy PEG (TMPEG) to form a PEGylated-α-Gal A. The PEGylated-α-Gal A is then purified to provide an isolated, PEGylated-α-Gal A.

SCHEMATIC OF REACTION

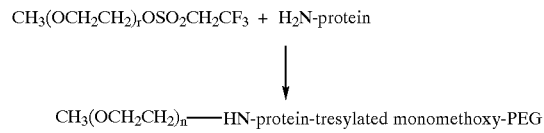

α-Gal A contains 18 amino groups, 17 ε-amino groups (lysine) and one α-amino group (N-terminus). The reaction can be controlled to produce α-Gal A with minimal substitutions and then molecules with one PEG per molecule, or a lesser mean number of PEG moieties per molecule, can be purified from the unsubstituted and multiply substituted forms. Multiple substitutions on α-Gal A may not significantly affect biological activity; therefore the final product may consist of a heterogeneous mixture of one to 18 attached PEG molecules. The level of substitution will depend on the level of retained enzymatic activity. It should be noted that a decrease in enzymatic activity can be offset by an enhanced therapeutic effect derived from lengthening the circulatory half-life and reducing immune recognition of α-Gal A. Thus, in developing a PEG-α-Gal A product, the ratio of PEG to α-Gal A should be dependent on biological activity, and not solely on enzymatic activity.

The PEGylation reaction requires a controlled pH, buffer composition, and protein concentration. Proper reaction conditions can be achieved by an ultrafiltration/diafiltration step, which is currently used in the manufacturing process. Immediately before reacting, tresyl-PEG is quickly solubilized in water with continuous stirring. This solution is then added to the prepared α-Gal A and allowed to react for a controlled amount of time and at a controlled temperature (e.g., 2 hours at 250° C.). PEGylation can occur prior to the final purification process, which will eliminate adding steps to the purification procedure. After the coupling is complete, PEG-α-Gal A is processed by the remaining steps of the purification process. Performing the reaction before the Q column (anion exchange) allows for two purification steps to remove the reaction byproducts. Since PEG does not contain any negative charge, it will not be retained by the Q Sepharose®, and will elute in the void volume.

The amount of PEGylation can be measured by known techniques. For example, fluorescamine fluoresces when bound to α-amino and ε-amino groups of proteins. The percent loss in fluorescence after PEGylation correlates to the percentage of PEG bound to α-Gal A. Pierce's BCA assay for total protein can be used to determine protein concentration. The methylumbelliferyl-α-D-galactopyranoside (4-MUF-α-Gal) activity assay is used to evaluate the effect of PEG-α-Gal A enzymatic activity. α-Gal A contains M6P, which is required for uptake into lysosomes. Interference from PEG on M6P receptor recognition can be evaluated using a cell-based assay to monitor cellular uptake of PEG-α-Gal A into lysosomes.

Methods of Administration of α-Gal A Preparation

Compositions of the present invention (i.e., comprising various α-Gal A glycoforms) may be administered by any route which is compatible with the α-Gal A preparation. The purified α-Gal A preparation can be administered to individuals who produce insufficient or defective α-Gal A protein or who may benefit from α-Gal A therapy. Therapeutic preparations of the present invention may be provided to an individual by any suitable means, directly (e.g., locally, as by injection, implantation or topical administration to a tissue locus) or systemically (e.g., orally or parenterally).

The route of administration may be oral or parenteral, including intravenous, subcutaneous, intra-arterial, intraperitoneal, ophthalmic, intramuscular, buccal, rectal, vaginal, intraorbital, intracerebral, intradermal, intracranial, intraspinal, intraventricular, intrathecal, intracisternal, intracapsular, intrapulmonary, intranasal, transmucosal, transdermal, or via inhalation. Intrapulmonary delivery methods, apparatus and drug preparation are described, for example, in U.S. Pat. Nos. 5,785,049, 5,780,019, and 5,775,320, each incorporated herein by reference. A preferred method of intradermal delivery is by iontophoretic delivery via patches; one example of such delivery is taught in U.S. Pat. No. 5,843,015, which is incorporated herein by reference.

A particularly useful route of administration is by subcutaneous injection. An α-Gal A preparation of the present invention is formulated such that the total required dose may be administered in a single injection of one or two milliliters. In order to allow an injection volume of one or two milliliters, an α-Gal A preparation of the present invention may be formulated at a concentration in which the preferred dose is delivered in a volume of one to two milliliters, or the α-Gal A preparation may be formulated in a lyophilized form, which is reconstituted in water or an appropriate physiologically compatible buffer prior to administration. Subcutaneous injections of α-Gal A preparations have the advantages of being convenient for the patient, in particular by allowing self-administration, while also resulting in a prolonged plasma half-life as compared to, for example, intravenous administration. A prolongation in plasma half-life results in maintenance of effective plasma α-Gal A levels over longer time periods, the benefit of which is to increase the exposure of clinically affected tissues to the injected α-Gal A and, as a result, increase the uptake of a α-Gal A into such tissues. This allows a more beneficial effect to the patient and/or a reduction in the frequency of administration. Furthermore, a variety of devices designed for patient convenience, such as refillable injection pens and needle-less injection devices, may be used with the α-Gal A preparations of the present invention as discussed herein.

Administration may be by periodic injections of a bolus of the preparation, or may be administered by intravenous or intraperitoneal administration from a reservoir which is external (e.g., an IV bag) or internal (e.g., a bioerodable implant, a bioartificial organ, or a population of implanted α-Gal A production cells). See, e.g., U.S. Pat. Nos. 4,407,957 and 5,798,113, each incorporated herein by reference. Intrapulmonary delivery methods and apparatus are described, for example, in U.S. Pat. Nos. 5,654,007, 5,780,014, and 5,814,607, each incorporated herein by reference. Other useful parenteral delivery systems include ethylene-vinyl acetate copolymer particles, osmotic pumps, implantable infusion systems, pump delivery, encapsulated cell delivery, liposomal delivery, needle-delivered injection, needle-less injection, nebulizer, aeorosolizer, electroporation, and transdermal patch. Needle-less injector devices are described in U.S. Pat. Nos. 5,879,327; 5520,639; 5,846,233 and 5,704,911, the specifications of which are herein incorporated by reference. Any of the α-Gal A preparation described above can administered in these methods.

The route of administration and the amount of protein delivered can be determined by factors that are well within the ability of skilled artisans to assess. Furthermore, skilled artisans are aware that the route of administration and dosage of a therapeutic protein may be varied for a given patient until a therapeutic dosage level is obtained.

Pharmaceutical Formulation of α-Gal A Protein

This invention further provides novel formulations of an α-Gal A preparation that are substantially free of non-α-Gal A proteins, such as albumin, non-α-Gal A proteins produced by the host cell, or proteins isolated from animal tissue or fluid.

The preparation preferably comprises part of an aqueous or physiologically compatible fluid suspension or solution. The carrier or vehicle is physiologically compatible so that, in addition to delivery of the desired preparation to the patient, it does not otherwise adversely affect the patient's electrolyte and/or volume balance. Useful solutions for parenteral administration may be prepared by any of the methods well known in the pharmaceutical art. See, e.g., REMINGTON'S PHARMACEUTICAL SCIENCES (Gennaro, A., ed.), Mack Pub., 1990. Non-parenteral formulations, such as suppositories and oral formulations, can also be used.

Preferably the formulation contains an excipient. Pharmaceutically acceptable excipients for α-Gal A which may be included in the formulation are buffers such as citrate buffer, phosphate buffer, acetate buffer, and bicarbonate buffer, amino acids, urea, alcohols, ascorbic acid, phospholipids; proteins, such as serum albumin, collagen, and gelatin; salts such as EDTA or EGTA, and sodium chloride; liposomes; polyvinylpyrollidone; sugars, such as dextran, mannitol, sorbitol, and glycerol; propylene glycol and polyethylene glycol (e.g., PEG-4000, PEG-6000); glycerol; glycine or other amino acids; and lipids. Buffer systems for use with α-Gal A preparations include citrate; acetate; bicarbonate; and phosphate buffers (all available from Sigma). Phosphate buffer is a preferred embodiment. A preferred pH range for α-Gal A preparations is pH 4.5–7.4.

The formulation also preferably contains a non-ionic detergent. Preferred non-ionic detergents include Polysorbate 20, Polysorbate 80, Triton X-100, Triton X-114, Nonidet P-40, Octyl α-glucoside, Octyl β-glucoside, Brij 35, Pluronic, and Tween 20 (all available from Sigma).

A particularly preferred formulation contains Polysorbate 20 or Polysorbate 80 non-ionic detergent and phosphate-buffered saline, most preferably at pH 6.

For lyophilization of α-Gal A preparations, the protein concentration can be 0.1–10 mg/mL. Bulking agents, such as glycine, mannitol, albumin, and dextran, can be added to the lyophilization mixture. In addition, possible cryoprotectants, such as disaccharides, amino acids, and PEG, can be added to the lyophilization mixture. Any of the buffers, excipients, and detergents listed above, can also be added.

In a preferred formulation α-Gal A for injection is at a concentration of 1 mg/mL Formulations for administration may include glycerol and other compositions of high viscosity to help maintain the agent at the desired locus. Biocompatible polymers, preferably bioresorbable, biocompatible polymers (including, e.g., hyaluronic acid, collagen, polybutyrate, lactide, and glycolide polymers and lactide/glycolide copolymers) may be useful excipients to control the release of the agent in vivo. Formulations for parenteral administration may include glycocholate for buccal administration, methoxysalicylate for rectal administration, or cutric acid for vaginal administration. Suppositories for rectal administration may be prepared by mixing an α-Gal A preparation of the invention with a non-irritating excipient such as cocoa butter or other compositions that are solid at room temperature and liquid at body temperatures.

Formulations for inhalation administration may contain lactose or other excipients, or may be aqueous solutions which may contain polyoxyethylene-9-lauryl ether, glycocholate or deoxycocholate. A preferred inhalation aerosol is characterized by having particles of small mass density and large size. Particles with mass densities less than 0.4 gram per cubic centimeter and mean diameters exceeding 5 µm efficiently deliver inhaled therapeutics into the systemic circulation. Such particles are inspired deep into the lungs and escape the lungs' natural clearance mechanisms until the inhaled particles deliver their therapeutic payload. (Edwards et al., Science 276: 1868–1872 (1997)). α-Gal A preparations of the present invention can be administered in aerosolized form, for example by using methods of preparation and formulations as described in, U.S. Pat. Nos. 5,654,007, 5,780,014, and 5,814,607, each incorporated herein by reference. Formulation for intranasal administration may include oily solutions for administration in the form of nasal drops, or as a gel to be applied intranasally.

Formulations for topical administration to the skin surface may be prepared by dispersing the α-Gal A preparation with a dermatological acceptable carrier such as a lotion, cream, ointment, or soap. Particularly useful are carriers capable of forming a film or layer over the skin to localize application and inhibit removal. For topical administration to internal tissue surfaces, the α-Gal A preparation may be dispersed in a liquid tissue adhesive or other substance known to enhance adsorption to a tissue surface. For example, several mucosal adhesives and buccal tablets have been described for transmucosal drug delivery, such as in U.S. Pat. Nos. 4,740,365, 4,764,378, and 5,780,045, each incorporated herein by reference. Hydroxypropylcellulose or fibrinogen/thrombin solutions may also be incorporated. Alternatively, tissue-coating solutions, such as pectin-containing formulations may be used.

The preparations of the invention may be provided in containers suitable for maintaining sterility, protecting the activity of the active ingredients during proper distribution and storage, and providing convenient and effective accessibility of the preparation for administration to a patient. An injectable formulation of an α-Gal A preparation might be supplied in a stoppered vial suitable for withdrawal of the contents using a needle and syringe. The vial would be intended for either single use or multiple uses. The preparation can also be supplied as a prefilled syringe. In some instances, the contents would be supplied in liquid formulation, while in others they would be supplied in a dry or lyophilized state, which in some instances would require reconstitution with a standard or a supplied diluent to a liquid state. Where the preparation is supplied as a liquid for intravenous administration, it might be provided in a sterile bag or container suitable for connection to an intravenous administration line or catheter. In preferred embodiments, the preparations of the invention are supplied in either liquid or powdered formulations in devices which conveniently administer a predetermined dose of the preparation; examples of such devices include a needle-less injector for either subcutaneous or intramuscular injection, and a metered aerosol delivery device. In other instances, the preparation may be supplied in a form suitable for sustained release, such as in a patch or dressing to be applied to the skin for transdermal administration, or via erodible devices for transmucosal administration. In instances where the preparation is orally administered in tablet or pill form, the preparation might be supplied in a bottle with a removable cover. The containers may be labeled with information such as the type of preparation, the name of the manufacturer or distributor, the indication, the suggested dosage, instructions for proper storage, or instructions for administration.

Dosages for Administration of α-Gal A Preparation

The present invention further provides methods for administering an α-Gal A preparation to a patient with Fabry disease, atypical variant of Fabry disease or any condition in which a reduced level or mutant form of α-Gal A is present. The dose of administration is preferably 0.05–5.0 mg, more preferably between 0.1–0.3 mg, of the α-Gal A preparation per kilogram body weight and is administered weekly or biweekly. In a preferred embodiment, a dose of about 0.2 mg/kg is administered biweekly. Regularly repeated doses of the protein are necessary over the life of the patient. Subcutaneous injections can be used to maintain longer term systemic exposure to the drug. The subcutaneous dosage can be between 0.01–10.0 mg, preferably 0. 1–5.0 mg, of the α-Gal A preparation per kg body weight biweekly or weekly. Dosages of α-Gal A preparations that are administered by intramuscular injections may be the same or different than those injected subcutaneously; in a preferred embodiment, intramuscular dosages are smaller and administered less frequently. The α-Gal A preparation can also be administered intravenously, e.g., in a intravenous bolus injection, in a slow push intravenous injection, or by continuous intravenous injection. Continuous IV infusion (e.g., over 2–6 hours) allows the maintenance of specific levels in the blood.

An alternative preferred method for administering an α-Gal A preparation to a patient involves administering a preferred dose of an α-Gal A preparation weekly or biweekly for a period of several years, e.g., up to three years, during which time a patient is monitored clinically to evaluate the status of his or her disease. Clinical improvement measured by, for example, improvement in renal or cardiac function or patient's overall well-being (e.g., pain), and laboratory improvement measured by, for example, reductions in urine, plasma, or tissue CTH levels, may be used to assess the patient's health status. In the event that clinical improvement is observed after this treatment and monitoring period, the frequency of α-Gal A administration may be reduced. For example, a patient receiving weekly injections of an α-Gal A preparation may change to biweekly injections. Alternatively, a patient receiving biweekly injections of an α-Gal A preparation may switch to monthly injections. Following such a change in dosing frequency, the patient should be monitored for another several years, e.g., a three year period, in order to assess Fabry disease-related clinical and laboratory measures. In a preferred embodiment, the administered dose does not change if a change in dosing frequency is made. This ensures that certain pharmacokinetic parameters (e.g. maximal plasma concentration [$C_{max}$], time to maximal plasma concentration [$t_{max}$], plasma, half-life [$t_{1/2}$], and exposure as measured by area under the curve [AUC]) remain relatively constant following each administered dose. Maintenance of these pharmacokinetic parameters will result in relatively constant levels of receptor-mediated uptake of α-Gal A into tissues as dose frequencies change.

A patient with atypical variant of Fabry disease, e.g., exhibiting predominantly cardiovascular abnormalities or renal involvement, is treated with these same dosage regiments, i.e., from 0.05 mg/kg to 5 mg/kg weekly or biweekly. The dose is adjusted as needed. For example, a patient with the cardiac variant phenotype who is treated with α-galactosidase A enzyme replacement therapy will have a change in the composition of their heart and improved cardiac function following therapy. This change can be measured with standard echocardiography which is able to detect increased left ventricular wall thickness in patients with Fabry disease (Goldman et al., *J Am Coll Cardiol* 7: 1157–1161 (1986)). Serial echocardiographic measurements of left ventricular wall thickness can be conducted during therapy, and a decrease in ventricular wall size is indicative of a therapeutic response. Patients undergoing α-gal A enzyme replacement therapy can also be followed with cardiac magnetic resonance imaging (MRI). MRI has the capability to assess the relative composition of a given tissue. For example, cardiac MRI in patients with Fabry disease reveals deposited lipid within the myocardium compared with control patients (Matsui et al., *Am Heart J* 117: 472–474, (1989)). Serial cardiac MRI evaluations in a patient undergoing enzyme replacement therapy can reveal a change in the lipid deposition within a patient's heart. Patients with the renal variant phenotype can also benefit from u:-galactosidase A enzyme replacement therapy. The effect of therapy can be measured by standard tests of renal function, such as 24-hour urine protein level, creatinine clearance, and glomerular filtration rate. The following Examples are presented in order to more fully illustrate the preferred embodiments of the invention. These Examples should in no way be construed as limiting the scope of the invention, as defined by the appended claims.

EXAMPLE 1

Preparation and Use of Constructs Designed to Deliver and Express α-Gal A

Two expression plasmids, pXAG-16 and pXAG-28, were constructed. These plasmids contain human α-Gal A cDNA encoding the 398 amino acids of the α-Gal A enzyme (without the α-Gal A signal peptide); the human growth hormone (hGH) signal peptide genomic DNA sequence, which is interrupted by the first intron of the hGH gene; and the 3' untranslated sequence (UTS) of the hGH gene, which contains a signal for polyadenylation. Plasmid pXAG-16 has the human cytomegalovirus immediate-early (CMV IE) promoter and first intron (flanked by non-coding exon sequences), while pXAG-28 is driven by the collagen Iα2 promoter and exon 1, and also contains the β-actin gene's 5' UTS, which contains the first intron of the β-actin gene.

Cloning of the Complete α-Gal A cDNA, and Construction of the α-Gal A Expression Plasmid pXAG-16

The human α-Gal cDNA was cloned from a human fibroblast cDNA library that was constructed as follows. Poly-A⁺ mRNA was isolated from total RNA, and cDNA synthesis was performed using reagents for the lambda ZapII® system according to the manufacturer's instructions (Stratagene Inc., LaJolla, Calif.). Briefly, "first strand" cDNA was generated by reverse transcription in the presence of an oligo-dT primer containing an internal XhoI restriction endonuclease site. Following treatment with RNase H, the cDNA was nick-translated with DNA polymerase I to generate double stranded cDNA. This cDNA was made blunt-ended with T4 DNA polymerase, and ligated to EcoRI adaptors. The products of this ligation were treated with T4 DNA kinase and digested with XhoI. The cDNA was fractionated by Sephacryl®-400 chromatography. Large and medium size fractions were pooled and the cDNAs ligated to EcoRI and XhoI-digested Lambda ZapII arms. The products of this ligation were then packaged and titered. The primary library had a titer of 1.2×10⁷ pfu/mL and an average insert size of 925 bp.

A 210 bp probe from exon 7 of the human α-Gal A gene (FIG. 1, SEQ ID NO:1) was used to isolate the cDNA. The probe itself was isolated from genomic DNA by the polymerase chain reaction (PCR) using the following oligonucleotides:

5'-CTGGGCTGTAGCTATGATAAAC-3' (Oligo 1; SEQ ID NO:6) and

5'-TCTAGCTGAAGCAAAACAGTG-3' (Oligo 2; SEQ ID NO:7).

The PCR product was then used to screen the fibroblast cDNA library, and positive clones were isolated and further characterized. One positive clone, phage 3A, was subjected to the lambda ZapII® system excision protocol (Stratagene, Inc., La Jolla, Calif.), according to the manufacturer's instructions. This procedure yielded plasmid pBSAG3A, which contains the α-Gal A cDNA sequence in the pBluescriptSK-™ plasmid backbone. DNA sequencing revealed that this plasmid did not contain the complete 5' end of the cDNA sequence. Therefore, the 5' end was reconstructed using a PCR fragment amplified from human genomic DNA. To accomplish this, a 268 bp genomic DNA fragment (FIG. 2, SEQ ID NO:2) was amplified using the following oligonucleotides: 5'-ATTGGTCCGCCCCTGAGGT-3' (Oligo 3; SEQ ID NO:8) and 5'-TGATGCAGGAATCTGGCTCT-3' (Oligo 4; SEQ ID NO:9). This fragment was subcloned into a "TA" cloning plasmid (Invitrogen Corp., San Diego, Calif.) to generate plasmid pTAAGEI. Plasmid pBSAG3A, which contains the majority of the α-Gal A cDNA sequence, and pTAAGEI, which contains the 5' end of the α-Gal A cDNA, were each digested with SacII and NcoI. The positions of the relevant SacII and NcoI sites within the amplified DNA fragment are shown in FIG. 2. The 0.2 kb SacII-NcoI fragment from pTAAGEI was isolated and ligated to equivalently digested pBSAG3A. This plasmid, pAGAL, contains the complete α-Gal A cDNA sequence, including the sequence encoding the α-Gal A signal peptide. The cDNA was completely sequenced (shown in FIG. 3 including the α-Gal A signal peptide; SEQ ID NO:3) and found to be identical to the published sequence for the human α-Gal A cDNA (Genbank sequence HUMGALA).

The plasmid pXAG-16 was constructed via several intermediates, as follows. First, pAGAL was digested with SacII and XhoI and blunt-ended. Second, the ends of the complete α-Gal A cDNA were ligated to XbaI linkers and subcloned into XbaI digested pEF-BOS (Mizushima et al., *Nucl. Acids Res.* 18: 5322, 1990), creating pXAG-1. This construct contains the human granulocyte-colony stimulating factor (G-CSF) 3' UTS and the human elongation factor-1α (EF-1α) promoter flanking the cDNA encoding α-Gal A plus the α-Gal A signal peptide, such that the 5' end of the α-Gal A cDNA is fused to the EF-1α promoter. To create a construct with the CMV IE promoter and first intron, the α-Gal A cDNA and G-CSF 3' UTS were removed from pXAG-1 as a 2 kb XbaI-BamHI fragment. The fragment was blunt-ended, ligated to BamHI linkers, and inserted into BamHI digested pCMVflpNeo (which was constructed as described below). The orientation was such that the 5' end of the α-Gal A cDNA was fused to the CMV IE promoter region.

pCMVflpNeo was created as follows. A CMV IE gene promoter fragment was amplified by PCR using CMV genomic DNA as a template and the oligonucleotides: 5'-TTTTGGATCCCTCGAGGACATTGATTATTGACT AG-3' (SEQ ID NO:10) and 5'-TTTTGGATCCCGTGTCAAGGACGGTGAC-3' (SEQ ID NO:11).

The resulting product (a 1.6 kb fragment) was digested with BamHI, yielding a CMV promoter-containing fragment with cohesive BamHI-digested ends. The neo expression unit was isolated from plasmid pMC1neopA (Stratagene Inc., La Jolla, Calif.) as a 1.1 kb XhoI-BamHI fragment. The CMV promoter-containing and neo fragments were inserted into a BamHI-, XhoI-digested plasmid (pUC12). Notably, pCMVflpNeo contains the CMV IE promoter region, beginning at nucleotide 546 and ending at nucleotide 2105 (of Genbank sequence HS5MIEP), and the neomycin resistance gene driven by the Herpes Simplex Virus (HSV) thymidine kinase promoter (the TKneo gene) immediately 5' to the CMV IE promoter fragment. The direction of transcription of the neo gene is the same as that of the CMV promoter fragment. This intermediate construct was called pXAG-4.

To add the hGH 3' UTS, the GCSF 3' UTS was removed from pXAG-4 as an XbaI-SmaI fragment and the ends of pXAG-4 were made blunt. The hGH 3' UTS was removed from pXGH5 (Selden et al., *Mol. Cell. Biol.* 6: 3173–3179, 1986) as a 0.6 kb SmaI-EcoRI fragment. After blunt-ending this fragment, it was ligated into pXAG-4 immediately after the blunt-ended XbaI site of pXAG-4. This intermediate was called pXAG-7. The TKneo fragment was removed from this plasmid as a HindIII-ClaI fragment and the ends of the plasmid were blunted by "filling-in" with the Klenow fragment of DNA polymerase I. A neomycin resistance gene driven by the SV40 early promoter was ligated in as a blunted ClaI-BsmBI fragment from a digest of pcDNeo (Chen et al., *Mol. Cell. Biol.* 7: 2745–2752, 1987), placing the neo transcription unit in the same orientation as the α-Gal A transcription unit. This intermediate was called pXAG-13.

To complete pXAG-16, which has the 26 amino acid hGH signal peptide coding sequence and first intron of the hGH gene, a 2.0 kb EcoRI-BamHI fragment of pXAG-13 was first removed. This fragment included the α-Gal A cDNA and the hGH 3' UTS. This large fragment was replaced with 3 fragments. The first fragment consisted of a 0.3 kb PCR product of pXGH5, which contains the hGH signal peptide coding sequence and includes the hGH first intron sequence, from a synthetic BamHI site located just upstream of the Kozak consensus sequence to the end of the hGH signal peptide coding sequence. The following oligonucleotides were used to amplify this fragment (Fragment 1): 5'-TTTTGGATCCACCATGGCTA-3' (Oligo HGH101; SEQ ID NO:12) and 5'-TTTTGCCGGCACTGCCCTCTTGAA-3' (Oligo HGH102; SEQ ID NO:13). The second fragment consisted of a 0.27 kb PCR product containing sequences corresponding to the start of the cDNA encoding the 398 amino acid α-Gal A enzyme (i.e., lacking the α-Gal A signal peptide) to the NheI site. The following oligonucleotides were used to amplify this fragment (Fragment 2): 5'-TTTTCAGCTGGACAATGGATTGGC-3' (Oligo AG10; SEQ ID NO:14) and 5'-TTTTGCTAGCTGGCGAATCC-3' (Oligo AG11; SEQ ID NO:15). The third fragment consisted of the NheI-EcoRI fragment of pXAG-7 containing the remaining α-Gal A sequence as well as the hGH 3' UTS (Fragment 3).

Fragment 1 (digested with BamHI and NaeI), Fragment 2 (digested with PvuII and NheI), and Fragment 3 were mixed with the 6.5 kb BamHI-EcoRI fragment of pXAG-13 containing the neo gene and the CMV IE promoter and ligated together to generate plasmid pXAG-16 (FIG. 4).

1.2 Construction of the α-Gal A Expression Plasmid pXAG-28

The human collagen Iα2 promoter was isolated for use in the α-Gal A expression construct pXAG-28 as follows. A 408 bp PCR fragment of human genomic DNA containing part of the human collagen Iα2 promoter was isolated using the following oligonucleotides:

5'-TTTTGGATCCGTGTCCCATAGTGTTTCCAA-3' (Oligo 72; SEQ ID NO:16) and

5'-TTTTGGATCCGCAGTCGTGGCCAGTACC-3' (Oligo 73; SEQ ID NO:17).

This fragment was used to screen a human leukocyte library in EMBL3 (Clontech Inc., Palo Alto, Calif.). One positive clone (phage 7H) containing a 3.8 kb EcoRI fragment was isolated and cloned into pBSIISK+ (Stratagene Inc., La Jolla, Calif.) at the EcoRI site (creating pBS/7H.2). An AvrII site was introduced in pBSIISK+ by digesting with SpeI, which cleaves within the pBSIISK+ polylinker, "filling-in" with the Klenow fragment of DNA polymerase I, and inserting the oligonucleotide 5'-CTAGTCCTAGGA-3' (SEQ ID NO:18). This variant of pBSIISK+ was digested with BamHI and AvrII and ligated to the 121 bp BamHI-AvrII fragment of the original 408 bp collagen Iα2 promoter PCR fragment described above, creating pBS/121COL.6.

The plasmid pBS/121COL.6 was digested with XbaI, which cleaves within the pBSIISK+ polylinker sequence, "filled-in" with the Klenow fragment of DNA polymerase I, and digested with AvrII. The 3.8 kb BamHI-AvrII fragment of pBS/7H.2 was isolated and the BamHI site made blunt-ended by treatment with Klenow enzyme. The fragment was then digested with AvrII and ligated to the AvrII-digested vector, thus creating the collagen promoter plasmid pBS/121bpCOL7H.18.

Next the collagen promoter was fused to the 5' UTS of the human β-actin gene, which contains the first intron of the human β-actin gene. To isolate this sequence, a 2 kb PCR fragment was isolated from human genomic DNA using the following oligonucleotides:

5'-TTTTGAGCACAGAGCCTCGCCT-3' (Oligo BA1; SEQ ID NO:19) and

5'-TTTTGGATCCGGTGAGCTGCGAGAATAGCC-3' (Oligo BA2; SEQ ID NO:20).

This fragment was digested with BamHI and BsiHKAI to release a 0.8 kb fragment containing the β-actin 5' UTS and intron. A 3.6 kb SalI-SrfI fragment was then isolated from the collagen promoter plasmid pBS/121bpCOL7H.18 as follows. pBS/121bpCOL7H.18 was partially digested with BamHI (the BamHI site lies at the 5' end of the collagen Iα2 promoter fragment), made blunt-ended by treatment with the Klenow fragment, and ligated to a SalI linker (5'-GGTCGACC-3'), thereby placing a SalI site upstream of the collagen Iα2 promoter. This plasmid was then digested with SalI and SrfI (the SrfI site lies 110 bp upstream of the collagen Iα2 promoter CAP site), and the 3.6 kb fragment was isolated. The 0.8 and 3.6 kb fragments were combined with SalI- and BamHI-digested pBSIISK- (Stratagene Inc., La Jolla, Calif.), and a fragment composed of the following four oligonucleotides annealed together (forming a fragment with a blunt end and a BsiHKAI end):

5'-GGGCCCCCAGCCCCAGCCCTCCCATTGGTG GAGGCCCTTTTGGAGGCAC CCTAGGGCCAGGAAACTTTTGCCGTAT-3' (Oligo COL-1; SEQ ID NO:21), 5'-AAATAGGGCAGATCCGGGCTTTATTATTTTA GCACCACGGCCGCCGAGA CCGCGTCCGCCCCGCGAGCA-3' (Oligo COL-2; SEQ ID NO:22), 5'-TGCCCTATTTATACGGCAAAAGTTTCCTGGC CCTAGGGTGCCTCCAAAA GGGC CTCCAC- CAATGGGAGGGCTGGGGCTGGGG GCCC-3' (Oligo COL-3; SEQ ID NO:23), and 5'-CGCGGGGCGGACGCGGTCTCGGCGGCCGT GGTGCTAAAATAATAAAGC CCGGATC-3' (Oligo COL-4; SEQ ID NO:24).

These four oligonucleotides, when annealed, correspond to the region beginning at the SrfI site of the collagen promoter and continuing through the BsiHKAI site of the β-actin promoter. The resulting plasmid was designated pCOL/β-actin.

Figure 5:
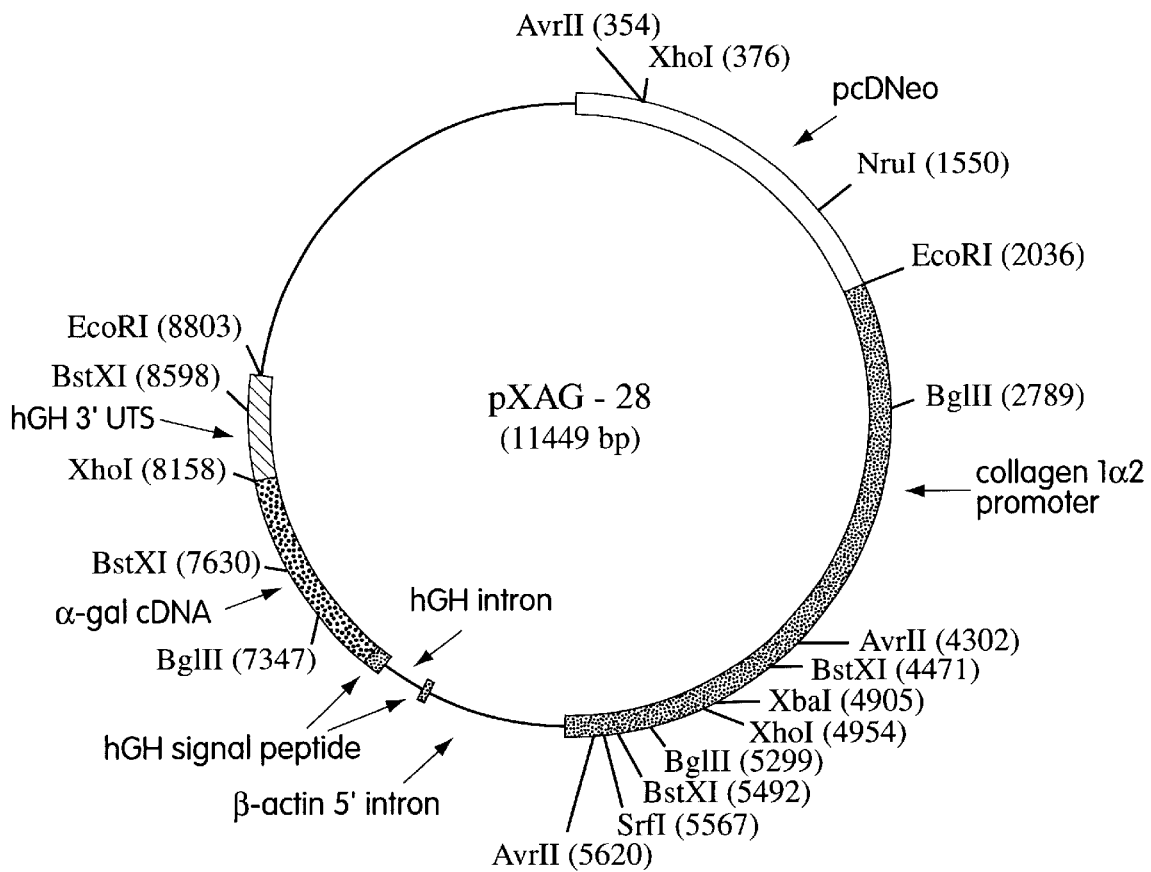
FIG. 5 is a schematic map of pXAG-28, an α-Gal A expression construct that includes the collagen Iα2 promoter and first exon, a β-actin intron, the hGH signal peptide coding sequence and first intron, the cDNA for α-Gal A (lacking the α-Gal A signal peptide sequence) and the hGH 3' UTS. pcDNeo indicates the position of the neo gene derived from plasmid pcDNeo.

To complete the construction of pXAG-28, the SalI-BamHII fragment of pCOL/β-actin, containing the collagen Iα2 promoter and β-actin 5' UTS, was isolated. This fragment was ligated to two fragments from pXAG-16 (see Example 1.1 and FIG. 4): (1) the 6.0 kb BamHI fragment (containing the neo gene, plasmid backbone, the cDNA encoding the 398 amino acid α-Gal A enzyme, and the hGH 3' UTS); and (2) the 0.3 kb BamHI-XhoI fragment (which contains the SV40 poly A sequence from pcDneo). pXAG-28 contains the human collagen Iα2 promoter fused to the human β-actin 5' UTS, the hGH signal peptide (which is interrupted by the hGH first intron), the cDNA encoding the α-Gal A enzyme, and the hGH 3' UTS. A map of the completed expression construct pXAG-28 is shown in FIG. 5.

1.3 Transfection and Selection of Fibroblasts Electroporated with α-Gal A Expression Plasmids In order to express α-Gal A in fibroblasts, secondary fibroblasts were cultured and transfected according to published procedures (Selden et al., WO 93/09222).

The plasmids pXAG-13, pXAG-16 and pXAG-28 were transfected by electroporation into human foreskin fibroblasts to generate stably transfected clonal cell strains, and the resulting α-Gal A expression levels were monitored as described in Example 1.4. Secretion of α-Gal A by normal foreskin fibroblasts is in the range of 2–10 units/$10^6$ cells/24 hours. In contrast, the transfected fibroblasts displayed mean expression levels as shown in Table 2.

TABLE 2

Mean α-Gal A expression levels (±standard deviation)

| | |
|---|---|
| pXAG-13: | 420 ± 344 U/$10^6$ cells/day |
| | N = 26 clonal strains |
| | (range 3–1133 U/$10^6$ cells/day) |
| pXAG-16: | 2,051 ± 1253 U/$10^6$ cells/day |
| | N = 24 clonal strains |
| | (range 422–5200 U/$10^6$ cells/day) |
| pXAG-28: | 141 ± 131 U/$10^6$ cells/day |
| | N = 38 clonal strains |
| | (range 20–616 U/$10^6$ cells/day) |

These data show that all three expression constructs are capable of increasing α-Gal A expression many times that of nontransfected fibroblasts. Expression by fibroblasts stably transfected with pXAG-13, which encodes α-Gal A linked to the α-Gal A signal peptide, was substantially lower than expression by fibroblasts transfected with pXAG-16, which differs only in that the signal peptide is the hGH signal peptide, the coding sequence of which is interrupted by the first intron of the hGH gene.

Each time the transfected cells were passaged, the secreted α-Gal A activity was determined, the cells were counted, and the cell density was calculated. Based on the number of cells harvested and the time allowed for secretion of α-Gal A, the specific expression rate of α-Gal A was determined and is reported in Tables 3 and 4 as secreted units (of α-Gal A) per $10^6$ cells per 24 hour period. Cell strains desirable for gene therapy or for use in generation of material for purification of α-Gal A should display stable growth and expression over several passages. Data from the cell strains shown in Tables 3 and 4, which were stably transfected with the α-Gal A expression construct pXAG-16, illustrate the fact that α-Gal A expression is stably maintained during serial passage.

TABLE 3

Growth and Expression of BRS-11 Cells Containing the α-Gal A Expression Construct pXAG-16

| Passage | Expression (units/$10^6$ cells/24 hr) | Cell Density (cells/cm$^2$) |
|---|---|---|
| 13 | 2601 | 4.80 × $10^4$ |
| 14 | 1616 | 4.40 × $10^4$ |
| 15 | 3595 | 4.40 × $10^4$ |

TABLE 4

Growth and Expression of HF503-242 Cells Containing the α-Gal A Expression Construct PxAG-16

| Passage | Expression (units/$10^6$ cells/24 hr) | Cell Density (cells/cm$^2$) |
|---|---|---|
| 5 | 4069 | 2.80 × $10^4$ |
| 6 | 7585 | 3.55 × $10^4$ |
| 7 | 5034 | 2.48 × $10^4$ |

1.4 Quantification of α-Gal A Expression

The activity of α-Gal A activity was measured using the water-soluble substrate 4-methylumbelliferyl-α-D-galactopyranoside (4-MUF-gal; Research Products, Inc.) by a modification of protocol described by Ioannou et al., *J. Cell Biol.* 119: 1137–1150 (1992). The substrate was dissolved in substrate buffer (0.1 M citrate-phosphate, pH 4.6) to a concentration of 1.69 mg/mL (5 mM). Typically, 10 mL of culture supernatant was added to 75 mL of the solution. The tubes were covered and allowed to incubate in a 37° C. water bath for 60 minutes. At the end of the incubation period, 2 mL of glycine-carbonate buffer (130 mM glycine, 83 mM sodium carbonate, at pH 10.6), were used to stop the reaction. The relative fluorescence of each sample was measured using a model TK0100 fluorometer (Hoefer Scientific Instruments) which has a fixed excitation wavelength of 365 nm and detects a fixed emission wavelength of 460 nm. The readings of the samples were compared to standards prepared from a 1 mM stock of methylumbelliferone (Sigma Chemical Co.), and the amount of hydrolyzed substrate was calculated. The activity of α-Gal A is expressed in units; one unit of α-Gal A activity is equivalent to one nanomole of substrate hydrolyzed per hour at 37° C. Cell expression data were generally expressed as units of α-Gal A activity secreted/$10^6$ cells/24 hours. This assay was also used to measure the amount of α-Gal activity in cell lysates and in samples from various α-Gal purification steps, as discussed below.

1.5 Preparation of Gene-Activated α-Gal A (GA-GAL)

Production of gene-activated α-Gal A (GA-GAL) occurred by insertion of regulatory and structural DNA sequences upstream of the human α-Gal A coding sequence, using the GA technology substantially as described in U.S. Pat. No. 5,733,761, herein incorporated by reference. The precise insertion of the gene-activating sequence occurs as a result of homologous recombination between DNA present on a transfected DNA fragment and genomic DNA sequences upstream of the α-Gal A locus in a human cell. The gene-activating sequence itself contains α-Gal A coding sequence up to, but not including, the signal peptide cleavage site. Cells containing an activated α-Gal A locus were isolated and subjected to drug selection to isolate cells with increased GA-GAL production.

Figure 9:
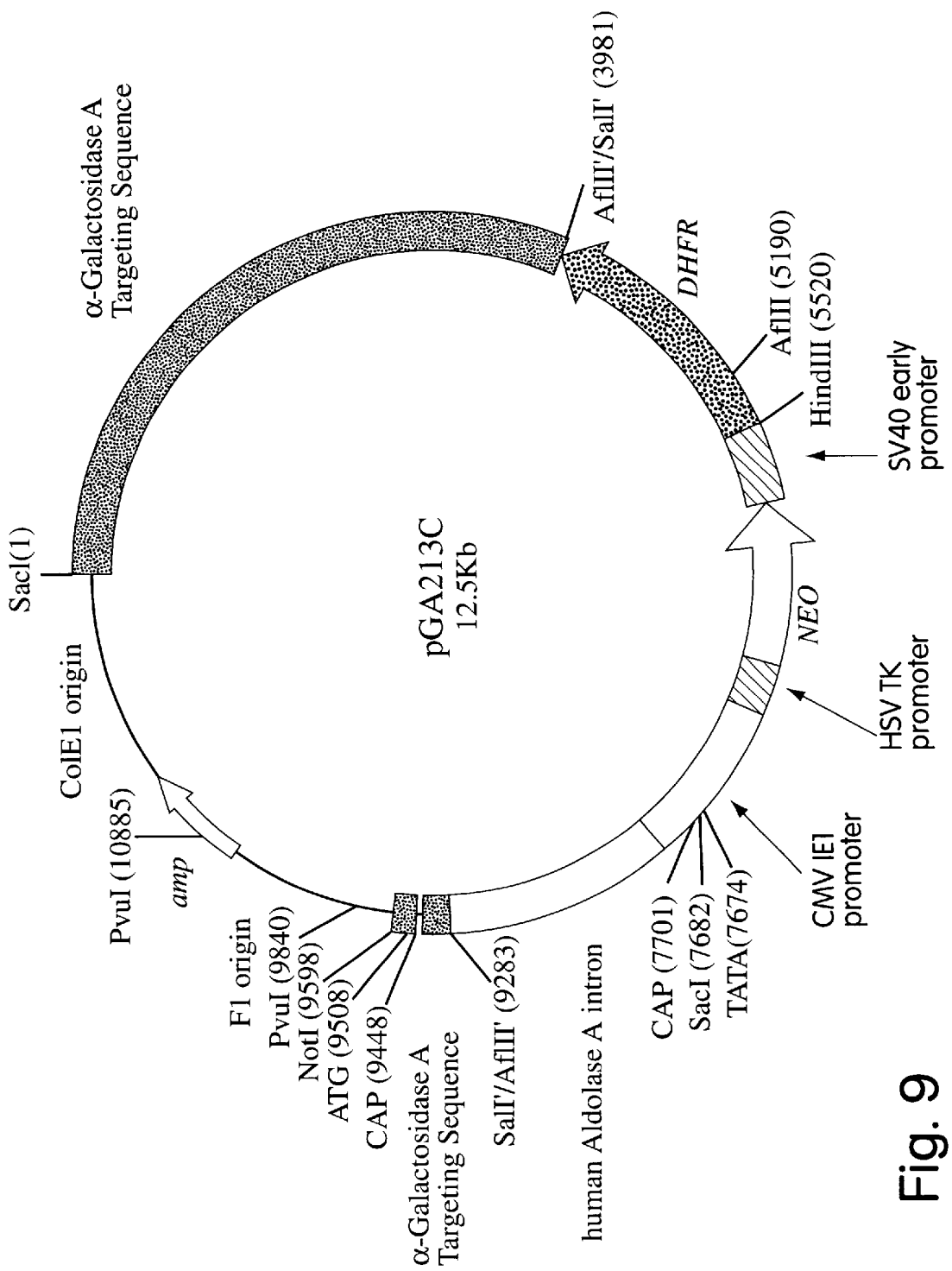
FIG. 9 is a schematic map of pGA213C.

A targeting DNA fragment containing an appropriate gene-activating sequence was introduced into host human cell lines by electroporation. One such cell line is HT-1080, a certified cell line available from ATCC (Rockville, Md.). The gene activation plasmid (targeting construct) pGA213C containing such a DNA fragment is shown in FIG. 9. This plasmid contains sequences designed to activate a portion of the endogenous α-Gal A locus in the host cell line, and contains sequences encoding the signal peptide, but not human α-Gal A. The targeting construct also contains expression cassettes for the bacterial neo and mouse dhfr genes. These allow for the selection of stably integrated targeting fragments (via the neo gene) and for subsequent selection of the dhfr gene using step-wise methotrexate (MTX) selection.

Figure 10:
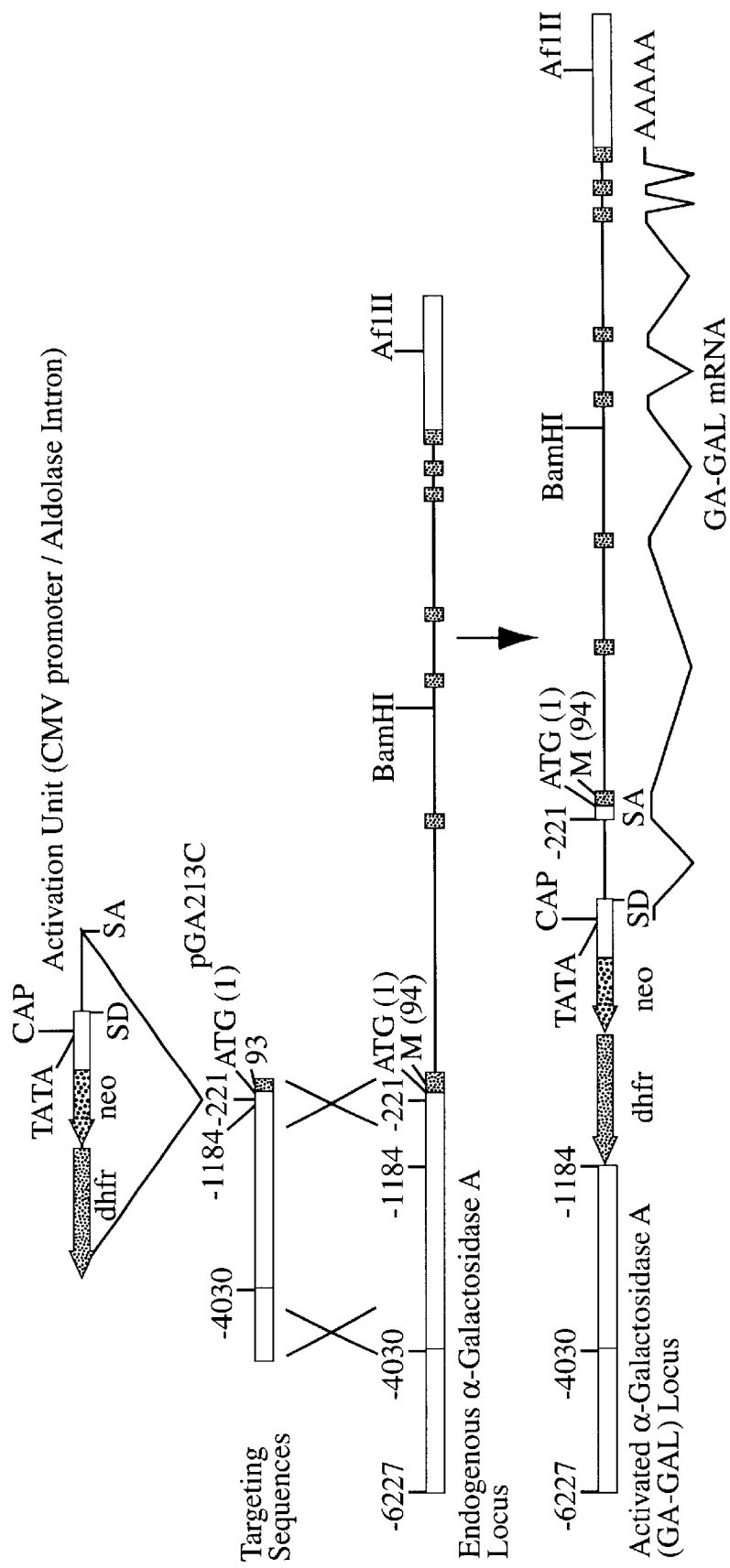
FIG. 10 is a diagrammatic representation of the targeting construct, pGA213C, and homologous recombination with the endogenous α-galactosidase A locus. pGA213C is depicted as targeting sequences aligned above corresponding sequences on the X-chromosomal α-galactosidase A locus. Positions relative to the methionine initiation codon, ATG, are indicated by the numbers above the linear maps. The activation unit containing murine dhfr, bacterial neo, and CMV promoter/aldolase intron sequences is shown above the position (−221) into which they were inserted by DNA cloning. α-galactosidase A coding sequences are indicated by the darkened boxes. α-galactosidase A non-coding genomic sequences are indicated by the lightly filled boxes. Large arrowheads indicate the direction of transcription for dhfr and neo expression cassettes. Splicing of the GA-GAL mRNA following successful targeting and gene activation is indicated by the segmented line below the map of the activated α-galactosidase A (GA-GAL) locus.

In addition, pGA213C contains sequences designed to target chromosomal sequences upstream of the endogenous α-Gal A locus by homologous recombination. Homologous recombination between the endogenous α-Gal A locus and the 9.6 kb DNA fragment of pGA213C is shown in FIG. 10.

pGA213C was constructed to delete 962 bp of genomic sequences extending from positions −1183 to −222 relative to the methionine initiation codon of α-Gal A, upon homologous recombination of the pGA213C fragment with the X-chromosomal α-Gal A locus. Transcriptional activation of the α-Gal A locus occurs through precise targeting of the exogenous regulatory sequences upstream of the α-Gal A coding region. The resulting GA-GAL locus cause transcription to initiate from the CMV promoter and to proceed through CMV exon 1, the aldolase intron and the seven exons and six introns of the α-Gal A coding sequence. Splicing of the large precursor mRNA joins the exogenous CMV exon (inserted by targeting) with the entire endogenous first exon of α-Gal A transcript. Translation of the GA-GAL mRNA results in pre GA-GAL with a thirty one amino acid signal peptide. Upon secretion from the host cell, the signal peptide is removed. Correctly targeted cell lines are first identified by polymerase chain reaction screening for the presence of the GA-GAL mRNA. Clones producing the GA-GAL mRNA are also found to secrete enzymatically active α-Gal A into the culture media. Subsequent confirmation of targeting events is accomplished by restriction enzyme digestion and Southern blot hybridization analysis of genomic DNA.

Cells were exposed to stepwise methotrexate ("MTX") selection. Following selection in 0.05 μM MTX, a clone of cells was isolated and subjected to 0.1 μM MTX selection. From this process a pool of cells resistant to 0.1 μM MTX was isolated (cell line RAG001), expanded in culture and characterized.

EXAMPLE 2

α-Gal A Purification

The following is a preferred method for producing, purifying, and testing α-Gal A. The purification process maintains α-Gal A in a soluble, active, native form throughout the purification process. The protein is not exposed to extremes of pH, organic solvents or detergents, is not proteolytically cleaved during the purification process, and does not form aggregates. The purification process is designed not to alter the distribution of α-Gal A glycoforms.

2.1 Purification of α-Gal A

Example 2.1 illustrates that α-Gal A may be purified to near-homogeneity from the conditioned medium of cultured human cell strains that have been stably transfected to produce the enzyme. α-Gal A is isolated from α-Gal A containing media using a series of five chromatographic steps. The five steps utilize various separation principles which take advantage of different physical properties of the enzyme to separate α-Gal A from contaminating material. Included are hydrophobic interaction chromatography on butyl Sepharose®, ionic interaction on hydroxyapatite, anion exchange chromatography on Q Sepharose®, and size exclusion chromatography on Superdex® 200. In addition to being the final step in the purification process, size exclusion chromatography also serves as an effective means to exchange the purified protein into a formulation-compatible buffer.

Figure 8:
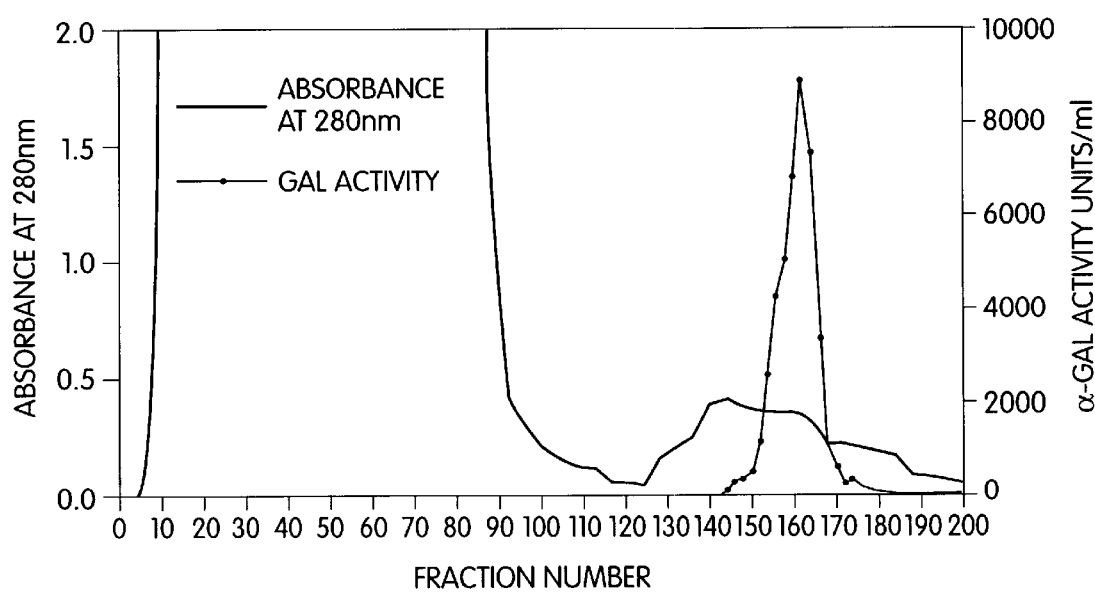
FIG. 8 is a chromatogram of the α-Gal A purification step using Butyl Sepharose® resin. The absorbance at 280 nm (plain line) and α-Gal A activity (dotted line) of selected fractions is shown.

A. Use of Butyl Sepharose® Chromatography as a First Step in the Purification of α-Gal A Cold conditioned medium (1.34 liters) was clarified by centrifugation and filtered through a 0.45 μm cellulose acetate filter using glass fiber prefilters. While stirring, the pH of the cold, filtered medium was adjusted to 5.6 by the dropwise addition of 1 N HCl, and ammonium sulfate was added to a final concentration of 0.66 M by the dropwise addition of a stock solution (room temperature) of 3.9 M ultrapure ammonium sulfate. The medium was stirred for an additional 5 minutes at 4° C, filtered as before, and applied to a Butyl Sepharose® 4 Fast Flow column (81 ml column volume, 2.5×16.5 cm; Pharmacia, Uppsala, Sweden) that had been equilibrated in 10 mM MES-Tris, pH 5.6, containing 0.66 M ammonium sulfate (buffer A). The chromatography was performed at 4° C. on a Gradi-Frac™ System (Pharmacia, Uppsala, Sweden) equipped with in-line UV (280 nm) and conductivity monitors for assessing total protein and salt concentration, respectively. After sample application at a flow rate of 10 ml/min, the column was washed with 10 column volumes of buffer A. The α-Gal A was eluted from the Butyl Sepharose® column with a 14 column volume linear gradient from buffer A (containing ammonium sulfate) to 10 mM MES-Tris, pH 5.6 (no ammonium sulfate). Fractions were assayed for α-Gal A activity by the 4-MUF-gal assay, and those containing appreciable enzyme activity were pooled. As seen in FIG. 8 and the purification summary (Table 5), this step removes approximately 99% of the contaminating protein (pre-column sample=8.14 g total protein; post-column sample=0.0638 g total protein).

TABLE 5

Purification of α-Gal A from the Conditioned Medium of Stably Transfected Human Fibroblasts

| Purification Step | Volume (ml) | α-Gal A Activity (× $10^6$ Units) | Total Protein (mg) | Specific Activity (× $10^6$ Units/mg) | Fold Purification (Cumulative) | Percent Recovery |
|---|---|---|---|---|---|---|
| Culture supernatant | 1340 | 14.6 | 8140 | 0.0018 | =1 | =100 |
| Buty Sepharose ® | 417 | 14.1 | 63.8 | 0.221 | 123 | 96.6 |
| Heparin Sepharose ® | 134 | 12.1 | 14.6 | 0.829 | 436 | 82.9 |
| Hydroxy-apatite | 47 | 9.73 | 4.46 | 2.18 | 1220 | 66.6 |
| Q Sepharose ® | 31.5 | 8.91 | 3.31 | 2.69 | 1503 | 61.0 |
| Superdex ® 200 | 10 | 8.58 | 2.93 | 2.92 | 1634 | 59.0 |

B. Use of Heparin Sepharose® Chromatography as a Step for Purification of α-Gal A The Butyl Sepharose® column peak fractions were dialyzed at 4° C. against (4 liters) of 10 mM MES-Tris, pH 5.6

(changed once). The conductivity of the dialysate was adjusted to 1.0 mMHO at 4° C. by addition of H$_2$O or NaCl as necessary. Afterward, the sample was applied to a column of Heparin Sepharose® 6 Fast Flow (Pharmacia, Uppsala, Sweden; 29 ml column volume, 2.5×6 cm) that had been equilibrated in 10 mM MES-Tris, pH 5.6, containing 9 mM NaCl (buffer B). This was done at 4° C. at a flow rate of 10 ml/min. In-line UV (280 nm) and conductivity monitors measured total protein and salt concentration. After the sample was applied, the column was washed with 10 column volumes of buffer B followed by a 3 column volume linear gradient to 8% buffer C/92% buffer B (where buffer C is 10 mM MES-Tris, pH 5.6, containing 250 mM NaCl) and a 10 column volume wash with 8% buffer C. This was followed by elution of α-gal A with a 1.5 column volume linear gradient to 29% buffer C and a subsequent 10 column volume linear gradient to 35% buffer C. Fractions were assayed for (x-gal A activity, and those containing appreciable activity were pooled.

C. Use of Hydroxyapatite Chromatography as a Step for Purification of α-Gal A

The heparin pool was filtered and applied directly to a column of Ceramic Hydroxyapatite HC (40 µm; American International Chemical, Natick, Mass.; 12 ml column volume, 1.5×6.8 cm) that had been equilibrated in 1 mM sodium phosphate, pH 6.0 (buffer D). The chromatography was performed at room temperature on a hybrid Gradi-Frac™/FPLC® System (Pharmacia, Uppsala, Sweden) equipped with in-line UV (280 nm) and conductivity monitors. After the sample was applied (5 ml/min), the column was washed with 10 column volumes of buffer D. The α-Gal A was eluted with a 7 column volume linear gradient to 42% buffer E/58% buffer D (where buffer E is 250 mM sodium phosphate, pH 6.0) followed by a 10 column volume gradient to 52% buffer E. Fractions were assayed for α-Gal A activity, and the fractions containing appreciable activity were pooled.

D. Use of Q Sepharose® Anion Exchange Chromatography as a Step for Purification of α-Gal A The hydroxyapatite pool was diluted approximately 1.5 fold with H$_2$O to a final conductivity of 3.4–3.6 mMHO at room temperature. After filtering, the sample was applied to a column of Q Sepharose® HP (Pharmacia, Uppsala, Sweden; 5.1 ml column volume, 1.5×2.9 cm) equilibrated in 10% buffer G/90% buffer F, where buffer F is 25 M sodium phosphate, pH 6.0, and buffer G is 25 mM sodium phosphate, pH 6.0, 250 mM NaCl. The chromatography was performed at room temperature on the Gradi-Frac™/FPLC® hybrid system (Pharmacia, Uppsala, Sweden), and total protein and salt concentrations were monitored by the in-line monitors. The sample was applied at a flow rate of 5 ml/min, then the following steps were performed: (1) a 5 column volume wash at 10% buffer G, (2) a 7 column volume wash at 12% buffer G, (3) a 3 column volume linear gradient to 50% buffer G, (4) a 10 column volume linear gradient to 53% buffer G, (5) a 3 column volume gradient to 100% buffer G, and (6) a 10 column volume wash at 100% buffer G. The α-Gal A eluted primarily during steps 3 and 4. Fractions containing appreciable activity were pooled (the "Q pool").

E. Use of Superdex(V-200 Gel Filtration Chromatography as a Step for Purification of α-Gal A The Q pool was concentrated approximately 5-fold using Centriprep®-10 centrifugal concentrator units (Amicon, Beverly, Mass.), and applied to a column of Superdex® 200 (Pharmacia, Uppsala, Sweden; 189 ml column volume, 1.6×94 cm). The column was equilibrated and eluted with 25 mM sodium phosphate, pH 6.0, containing 150 mM NaCl. The chromatography was performed on an FPLC® system (Pharmacia, Uppsala, Sweden) at room temperature using an in-line UV monitor (280 nm) to follow elution of the protein. The volume of the sample applied to the column was ≦2 ml, the flow rate was 0.5 ml/min, and the fraction size was 2 ml. Multiple column runs were performed; fractions were assayed for α-Gal A activity and fractions containing appreciable activity were pooled.

The pooled fractions from the Superdex® 200 column were concentrated using Centriprep 10 units, aliquoted, snap-frozen, and stored at −80° C. for short periods of time. A summary of this example of α-Gal A purification is shown in Table 5. The final yield of α-Gal A was 59% of the starting material activity, and the specific activity of the purified product was 2.92×10$^6$ units/mg protein. The resulting product showed a high level of purity after electrophoresis under reducing conditions on a 4–15% SDS-polyacrylamide gel, which was subsequently silver-stained.

SUMMARY

The purification process provides highly purified α-Gal A. The majority of the purification occurs in the first 2 steps of the process, while the final three steps serve to polish the material by removing the remaining minor contaminants. The last step, size exclusion chromatography on Superdex® 200, also serves to exchange the α-Gal A into a formulation-compatible buffer.

2.2 Size of α-Gal A Produced by Stably Transfected Human Cells in Culture

The structural and functional properties of purified human α-Gal A were investigated. The resulting product showed a high level of purity after electrophoresis under reducing conditions on a 4–15% SDS-polyacrylamide gel, which was subsequently silver-stained.

The molecular mass of α-Gal A was estimated by MALDI-TOF mass spectrometry. These results demonstrate that the molecular mass of the dimer is 102,353 Da, while that of the monomer is 51,002 Da. The expected molecular mass of the monomer, based on amino acid composition, is 45,400 Da. Therefore, the carbohydrate content of the enzyme accounts for up to 5,600 Da of the molecular weight.

2.3 Carbohydrate Modification of α-Gal A Produced by Stably Transfected Human Cells The glycosylation pattern of α-Gal A produced in accordance with the invention was also evaluated. Proper glycosylation is important for optimal in vivo activity of α-Gal A; α-Gal A expressed in non-glycosylating systems is inactive or unstable. Hantzopolous et al., *Gene* 57: 159 (1987). Glycosylation is also important for the internalization of α-Gal A into the desired target cells, and affects the circulating half-life of the enzyme in vivo. On each subunit of α-Gal A, there are four sites available for addition of asparagine-linked carbohydrate chains, of which only three are occupied. Desnick et al., In THE METABOLIC AND MOLECULAR BASES OF INHERITED DISEASE, (McGraw Hill, New York, 1995) pp 2741–2780.

A sample of α-Gal A produced by stably transfected cells was treated with neuraminidase, which is isolated from *A. urafaciens*, (Boehringer-Mannheim, Indianapolis, Ind.) to remove sialic acid. This reaction was performed by treating 5 mg of α-Gal A overnight with 10 mU of neuraminidase at room temperature in a total volume of 10 mL of acetate buffered saline (ABS, 20 mM sodium acetate, pH. 5.2, 150 mM NaCl).

Purified α-Gal A produced by stably transfected cells was also dephosphorylated using alkaline phosphatase (calf intestinal alkaline phosphatase, Boehringer-Mannheim, Indianapolis, Ind.), by treating 5 mg of α-Gal A overnight at room temperature with 15 U of alkaline phosphatase in ABS (pH raised to 7.5 with 1 M Tris).

The samples were analyzed by SDS-PAGE and/or isoelectric focusing followed by Western blotting with an anti-α-Gal A-specific antibody. The antibody used was a rabbit polyclonal anti-peptide antibody, which was produced using a peptide representing amino acids 68–81 of α-Gal A as an immunogen. Following transfer of the protein to PVDF (Millipore, Bedford, Mass.), the membrane was probed with a 1:2000 dilution of the anti-serum in 2.5% blotto (non-fat dry milk in 20 mM Tris-HCl, pH 7.5, 0.05% Tween-20). This was followed by detection with goat anti-rabbit IgG conjugated to horseradish peroxidase (Organo Technique/ Cappella, Durham, N.C.; 1:5000 dilution) and reagents of the ECL chemiluminescence kit (Amersham, Arlington Heights, Ind.).

Treatment of α-Gal A with neuraminidase followed by SDS-PAGE analysis resulted in a shift in molecular mass (approximately 1500–2000 Da or 4–6 sialic acids/ monomer), suggesting that there is extensive modification of α-Gal A with sialic acid. For reference, the plasma form of α-Gal A has 5–6 sialic acid residues per monomer, and the placental form has 0.5–1.0 sialic acid residues per monomer. Bishop et al., *J. Biol. Chem.* 256: 1307 (1981).

Another method used to examine the sialic acid and M6P modifications of α-Gal A was isoelectric focusing (IEF), where the samples are separated on the basis of their isoelectric point (pI) or net charge. Thus, removal of charged residues such as sialic acid or phosphate from α-Gal A would be expected to alter the mobility of the protein in the IEF system.

To perform the IEF experiment, samples of α-Gal A produced in accordance with the invention were treated with neuraminidase and/or alkaline phosphatase, mixed 1:1 with 2X Novex sample buffer (with 8 M urea, pH 3.0–7.0), and loaded onto a 6 M urea IEF gel (5.5% polyacrylamide) made using Pharmalyte® (Pharmacia, Uppsala, Sweden; pH 3.0–6.5; Pharmalyte® 4–6.5 and 2.5–5.5, 0.25 mL each per gel). Isoelectric point standards (Bio-Rad) were also included. Following electrophoresis, the gel was transferred to PVDF, and Western blot analysis performed as described above.

Neuraminidase treatment of the enzyme increased the pI of all three isoforms, indicating that all were modified to some extent by sialic acid. These data suggest that the α-Gal A preparations produced as described herein should have a desirable plasma half-life, indicating that this material is well suited for pharmacological use. Further, treatment of neuraminidase-treated α-Gal A with alkaline phosphatase further increased the pI of a portion of the protein to approximately 5.0–5.1, indicating that the enzyme bears one or more M6P residues. This modification is required for efficient internalization of α-Gal A by the target cells.

The N-linked carbohydrate chains of α-Gal A were analyzed by ion-exchange HPLC (Glyco-Sep C) and labeling of the non-reducing end with the fluorescent compound 2-amino benzamide (AB). The results of the analysis of AB-glycans from three separate α-Gal A preparations are summarized in Table 6. All three preparations had a Z number greater than 170. Further, over 67% of the glycans were sialylated, over 16% of the glycans were phosphorylated, and less than 16% were neutral. These results compared very favorably compared to results reported in the prior art. For example, Desnick et al., (U.S. Pat. No. 5,356,804) reported that over 60% of the glycans were neutral, with only 11% being sialylated.

TABLE 6

Results of Analysis of AB-glycans from GA-GAL

| Treatment | Z number | % Neutral | % Mono- | % Di- | % Tri- | % Tetra- |
|---|---|---|---|---|---|---|
| None | 170.04 | 16.83 | 22.8 | 39.45 | 15.34 | 5.58 |
| None | 177.71 | 14.22 | 20.63 | 44.62 | 14.2 | 6.31 |
| None | 171.68 | 15.81 | 20.73 | 43.2 | 14.33 | 5.39 |
| Mean (N = 3) | 173.14 | 15.62 | 21.39 | 42.42 | 14.62 | 5.76 |
| Neuraminidase | 24.36 | 85.25 | 5.14 | 9.61 | ND | ND |
| Alk. Phosphatase | 150.93 | 23.38 | 24.47 | 34.28 | 13.58 | 4.29 |

| Percent of Total: | GA-GAL preparations of the present invention | Desnick et al., U.S. Pat No. 5,356,804 |
|---|---|---|
| Total P-glycans | 16.62 | 24.1 |
| Total Sialylated | 67.57 | 11 |
| Total Neutral (hih-mannose and hybrid) | 15.62 | 62.9 |

Further detailed characterizations of the purified GA-GAL preparations are provided in Table 7.

TABLE 7

GA-GAL Purified Bulk

| Assay | 40-173-KH | 42-202-KH |
|---|---|---|
| Specific activity | 2.75 | 2.80 |
| SDS-PAGE Coomassie | 100% | 100% |
| SDS-PAGE Silver stain | 99.6% | 100% |
| Reverse phase HPLC | 100% | 99.94 |
| Size exclusion chromatography | 0% | 0.01% |
| Internalization by foreskin fibroblasts | 123.6% | 94.3% |

2.4 Increasing Proportion of Charged α-Gal A by fractionation of α-Gal A Species As discussed above, fractionation of α-Gal A glycoforms can occur at various steps in the purification process as described herein. In the present example, α-Gal A glycoforms were fractionated by size and by charge. It is also possible to fractionate α-Gal A by a combination of these or other chromatographic techniques as described above.

For size fractionation of α-Gal A glycoforms, size exclusion chromatography was performed on a Superdex® 200 column (Pharmacia, 1.6 cm by 94.1 cm) equilibrated in phosphate buffered saline at pH 6. α-Gal A (2.6 mg in 1 mL) was loaded onto the column, and the column was eluted at 0.35 mL/min. Fractions were collected across the elution profile, and the fractions comprising the broad elution peak of α-Gal A were analyzed by SDS-PAGE, then visualized with silver stain. The fractions at the leading edge of the peak contained α-Gal A of the highest molecular weight, and as the fractions continued across the peak, the apparent molecular weight of the α-Gal A gradually decreased. Fractions of α-Gal A were then selected and pooled to provide α-Gal A preparation of the desired molecular weight ranges.

For fractionation of α-Gal A glycoforms by charge, α-Gal A was fractionated by Q-Sepharose® chromatography. The Q-Sepharose® column (1.5 cm by 9.4 cm) was equilibrated in 20 mM sodium phosphate, pH 6.0, containing 30 mM NaCl and the flow rate was maintained at 5 mL/min. α-Gal A in (130 mg in 166 mL) was loaded onto the column, washed with equilibration buffer then eluted with 20 mM sodium phosphate, pH 6.0, containing 130 mM NaCl. For more extensive fractionation, a gradient elution (e.g., 10 column volumes) from the equilibration buffer to the elution buffer can be used. Fractions were collected across the elution profile, and the fractions comprising the elution peak of α-Gal A were analyzed by SDS-PAGE, then visualized by silver stain. The lowest molecular weight species observed on the gel eluted in the wash and at the leading edge of the peak, the highest molecular weight glycoforms eluted towards the end of the peak. The lower molecular weight species correspond to the less negatively charged glycoforms of α-Gal A, which bind less tightly to the positively charged Q-Sepharose® column (comprised of a quaternary amine substituted resin). The α-Gal A species of highest negative charge eluted later in the elution profile and have a higher molecular weight, as analyzed by SDS-PAGE. The fractionation by charge was confirmed by isoelectric focusing of the eluted fractions or of selected pools.

Thus, both the fractionation by size and the fractionation by charge permitted the selection of highly charged glycoforms of α-Gal A.

2.5 Mannose or Mannose-6-Phosphate (M6P) Mediated Internalization of α-Gal A

For the α-Gal A produced by stably transfected cells to be an effective therapeutic agent for α-Gal A deficiencies, the enzyme must be internalized by the affected cells. α-Gal A is minimally active at physiological pH levels, for example, in the blood or interstitial fluids. α-Gal A metabolizes accumulated lipid substrates optimally only when internalized in the acidic environment of the lysosome. This internalization is mediated by the binding of α-Gal A to M6P receptors, which are expressed on the cell surface and deliver the enzyme to the lysosome via the endocytic pathway. The M6P receptor is ubiquitously expressed; most somatic cells express M6P to some extent. The mannose receptor, which is specific for exposed mannose residues on glycoproteins, is less prevalent. The mannose receptors are generally found only on macrophage and macrophage-like cells, and provide an additional means of α-Gal A entry into these cell types.

In order to demonstrate M6P-mediated internalization of α-Gal A, skin fibroblasts from a Fabry disease patient (NIGMS Human Genetic Mutant Cell Repository) were cultured overnight in the presence of increasing concentrations of purified α-Gal A of the invention. Some of the samples contained 5 mM soluble M6P, which competitively inhibits binding to and internalization by the M6P receptor. Other samples contained 30 mg/mL mannan, which inhibits binding to and internalization by the mannose receptor. Following incubation, the cells were washed and harvested by scraping into lysis buffer (10 mM Tris, pH 7.2, 100 mM NaCl, 5 mM EDTA, 2 mM Pefabloc™ (Boehringer-Mannheim, Indianapolis, Ind.) and 1% NP-40). The lysed samples were then assayed for protein concentration and α-Gal A activity. The results are expressed as units of α-Gal A activity/mg cell protein. The Fabry cells internalized α-Gal A in a dose-dependent manner. This internalization was inhibited by M6P, but there was no inhibition with mannan. Therefore, internalization of α-Gal A in Fabry fibroblasts is mediated by the M6P receptor, but not by the mannose receptor.

α-Gal A is also internalized in vitro by endothelial cells, important target cells for the treatment of Fabry disease. Human umbilical vein endothelial cells (HUVECs) were cultured overnight with 7500 units of α-Gal A; some of the wells contained M6P. After the incubation period, cells were harvested and assayed for α-Gal A as described above. The cells incubated with α-Gal A had enzyme levels almost 10-fold those of control (no incubation with α-Gal A) cells. M6P inhibited the intracellular accumulation of α-Gal A, suggesting that the internalization of α-Gal A by HUVECs is mediated by the M6P receptor. Thus, the human α-Gal A of the invention is internalized by clinically relevant cells.

Few cultured human cell lines are known to express the mannose receptor. However, a mouse macrophage-like cell line (J774.E) which bears mannose receptors but few if any M6P receptors can be used to determine whether purified α-Gal A of the invention is internalized via the mannose receptor. Diment et al., *J. Leukocyte Biol.* 42: 485–490 (1987). J774.E cells were cultured overnight in the presence of 10,000 units/mL α-Gal A. Selected samples also contained 2 mM M6P, and others contained 100 mg/mL mannan. The cells were washed and harvested as described above, and the total protein and α-Gal A activity of each sample was determined. M6P does not inhibit the uptake of α-Gal A by these cells, while mannan decreases the accumulated α-Gal A levels by 75%. Thus, the α-Gal A of the invention may be internalized by the mannose receptor in cell types that express this particular cell surface receptor.

EXAMPLE 3

Pharmaceutical Formulation

Preparation of Buffer Solutions and Formulations

α-Gal A Purified Bulk is diluted to final concentration with α-Gal A Diluent. Based on the volume of purified bulk to be formulated, the concentration of α-Gal A (mg/mL), and the desired concentration of α-Gal A in the final formulation, the volume of α-Gal A diluent required is determined. α-Gal A diluent is prepared within 24 hours of use by mixing appropriate quantities of WFI, sodium chloride, and sodium phosphate monobasic, and adjusting the pH to 6.0 with sodium hydroxide solution. The composition of α-Gal A Diluent is listed in Table 8.

TABLE 8

| COMPOSITION OF αGAL A DILUENT (per Liter) | | |
|---|---|---|
| Component | Part Number | Quantity |
| Sodium chloride (USP) | 100-1916 | 8.8 g |
| Sodium hydroxide, 5N | 200-1903 | qs to adjust pH to 6.0 |
| Sodium phosphate, monobasic (USP) | 100-1913 | 3.5 g |
| Water for Injection (USP) | 100-2301 | qs ad 1.0 L |

One liter or smaller volumes of α-Gal A Diluent are filtered by vacuum filtration using sterile 0.2 mm nylon filters (Nalge Nunc International, Rochester, N.Y.). Larger volumes are filtered by positive pressure using a peristaltic pump and 0.2 mm Supor® capsule filters (Pall, Port Washington, N.Y.). All filters are subjected to post-filtration bubble point integrity testing. Mixing and filtration steps are performed in a certified Class 100 laminar flow hood. α-Gal A diluent is added to α-Gal A purified bulk in a mixing vessel to give a 1 mg/ml final solution. Then, the appropriate volume of polysorbate 20 (Tween 20, Spectrum) is added to reach a final concentration of 0.02%.

EXAMPLE 4

Desialylated Degalactosylated α-Gal A

To explore the effect of glycosylation on the biodistribution of α-Gal A, a purified preparation of α-Gal A was sequentially deglycosylated and each form injected into mice. The organs of the mice were collected at four hours post-injection and immunohistochemistry on the tissues performed to visualize possible changes in the biodistribution of the protein.

The α-Gal A was first treated with neuraminidase (sialidase) to remove sialic acid residues, leaving galactose moieties exposed. A portion of this sialidase-treated was further reacted with β-galactosidase to remove galactose residues; this left N-acetylglucosamine (GlcNAC) residues exposed. The GlcNACs were then removed by N-acetylglucosaminidase, leaving the core mannose groups on the protein. Untreated α-Gal A (control) or one of the treated forms of the protein were injected via the tail vein into mice. Four hours after the injections, the liver, spleen, heart, kidney and lungs from the mice were collected, preserved, and immunostained for detection of α-Gal A.

When compared to control animals receiving untreated protein, mice receiving the sialidase treated enzyme (galactose residues exposed) had more α-Gal A localized in the liver and correspondingly less of the enzyme in other examined organs. Additionally, the staining pattern in the liver was quite different. In control animals, the α-Gal A localized to primarily the Kupffer cells and endothelial cells with only moderate hepatocyte staining. In animals receiving the sialidase treated α-Gal A, the enzyme localized only to the hepatocytes, consistent with the known biodistribution of the asialoglycoprotein receptor. This effect of deglycosylation on the biodistribution was reversed when the galactose residues were removed by β-galactosidase. The staining pattern observed in the liver of the mice receiving this protein without galactose moieties was similar to that of the control animals; the majority of the staining was in Kupffer cells and endothelial cells, with minimal hepatocyte staining. Further treatment of the α-Gal A with N-acetylglucosaminidase did not alter the staining pattern from that observed for the β-galactosidase treated protein; that is, removal of the N-acetylglucosamine residues seemed to have little effect on the biodistribution of α-Gal A.

EXAMPLE 5

Correction of Fabry Fibroblasts by Human Fibroblasts Expressing α-Gal A

For gene therapy, an implant of autologous cells producing α-Gal A must produce the enzyme in a form modified appropriately to "correct" the α-Gal A deficiency in target cells. To assess the effect of α-Gal A production by transfected human fibroblasts on Fabry cells, fibroblasts harvested from Fabry disease patients (NIGMS Human Genetics Mutant Cell Repository) were co-cultured with an α-Gal A production cell strain (BRS-11) in Transwells® (Costar, Cambridge, Mass.). Fabry cells were cultured in 12-well tissue culture dishes, some of which contained inserts (Transwells®, 0.4 mm pore size) having a surface on which cells can be grown. The growth matrix of the insert is porous and allows macromolecules to pass from the upper to the lower milieu. One set of inserts contained normal human foreskin (HF) fibroblasts, which secrete minimal levels of α-Gal A, while another set contained the stably transfected human fibroblast strain, BRS-11, which secretes large amounts of α-Gal A. In the wells co-cultured with α-Gal A production cells, α-Gal A can enter the medium bathing the Fabry cells, and potentially be internalized by the Fabry cells.

The data in Table 9 show that Fabry cells internalized the secreted α-Gal A. The intracellular levels of α-Gal A were monitored for 3 days. Those cells cultured alone (no insert) or in the presence of non-transfected foreskin fibroblasts (HF insert) had very low intracellular levels of α-Gal A activity. The Fabry cells cultured with the α-Gal A production (BRS-11 insert) cells, however, exhibited enzyme levels similar to those of normal cells by the end of Day 2 (normal fibroblasts have 25–80 units α-Gal A/mg protein). That the correction is attributable to α-Gal A taken up via the M6P receptor is demonstrated by the inhibition with M6P (BRS-11 insert+M6P).

TABLE 9

CORRECTION OF FABRY FIBROBLASTS BY HUMAN FIBROBLASTS EXPRESSING αGal A ACTIVITY
(units/mg total protein)

| Time  | no insert | HF insert | BRS-11 insert | BRS-11 insert + M6P |
|-------|-----------|-----------|---------------|---------------------|
| Day 1 | 2 ± 1     | 2 ± 1     | 13 ± 1        | 4 ± 1               |
| Day 2 | 2 ± 1     | 2 ± 1     | 40 ± 11       | 6 ± 2               |
| Day 3 | 2 ± 1     | 5 ± 1     | 85 ± 1        | 9 ± 1               |

The foregoing description has been presented only for the purposes of illustration and is not intended to limit the invention to the precise form disclosed, but by the claims appended hereto. In the specification and the appended claims, the singular forms include plural references, unless the context clearly dictates otherwise. All patents and publications cited in this specification are incorporated by reference.

What is claimed is:

1. A human α-Gal A glycoprotein preparation, wherein greater than 50% of the total glycans of said preparation are complex-type glycans.

2. The human α-Gal A glycoprotein preparation of claim 1, wherein the preparation is purified to at least 98% homogeneity, as measured by SDS-PAGE or reverse phase HPLC.

3. The human α-Gal A glycoprotein preparation of claim 1, wherein the preparation has a specific activity of at least $2.0 \times 10^6$ units/mg protein.

4. The human α-Gal A glycoprotein preparation of claim 1, wherein the preparation is purified to at least 98% homogeneity, as measured by SDS-PAGE or reverse phase HPLC, and has a specific activity of at least $2.0 \times 10^6$ units/mg protein.

5. The human α-Gal A glycoprotein preparation of claim 1, wherein at least 67% of the total glycans of said preparation are complex-type glycans.

6. The human α-Gal A glycoprotein preparation of claim 1, wherein the composition comprises an average of two complex glycans per α-Gal A monomer.

7. The human α-Gal A glycoprotein preparation of claim 1, wherein more than 50% of the total glycans of the α-Gal A glycoforms are sialylated.

8. The human α-Gal A glycoprotein preparation of claim 1, wherein the α-Gal A is isolated from human cells transfected with an α-Gal A/mammalian expression vector construct.

9. The human α-Gal A glycoprotein preparation of claim 8, wherein the transfected human cells are secondary fibroblasts.

10. The composition of claim 1, wherein the α-Gal A glycoforms are comprised of between approximately 50% to 70% complex glycans with 2–4 sialic acid residues.

11. A composition comprising one or more mature, post-translationally-modified human α-Gal A glycoforms, purified to at least 98% homogeneity and having a specific activity of at least $2.0 \times 10^6$ units/mg protein, produced by separating the α-Gal A glycoforms from other components on a hydrophobic interaction resin, wherein the composition comprises greater than 50% complex glycans per α-Gal A glycoform.

12. The composition of claim 11, wherein at least 67% of the total glycans of said preparation are complex-type glycans.

13. The composition of claim 11, wherein the composition comprises an average of two complex glycans per α-Gal A monomer.

14. A composition comprising one or more mature, post-translationally-modifed human α-Gal A glycoforms, purified to at least 98% homogeneity and having a specific activity of at least $2.0 \times 10^6$ units/mg protein, wherein the composition comprises greater than 50% complex glycans per α-Gal A glycoform, produced by the following steps:

(a) binding the α-Gal A glycoforms to a cation exchange resin at acidic pH in an equilibration buffer, (b) washing the resin with the equilibration buffer to elute the unbound material, and (c) eluting the α-Gal A glycoforms using an elution solution selected from the group consisting of a salt solution of 10–100 mM, a buffered solution of pH 4–5, and combinations thereof.

15. The composition of claim 14, wherein at least 67% of the total glycans of said preparation are complex-type glycans.

16. The composition of claim 14, wherein the composition comprises an average of two complex glycans per α-Gal A monomer.

17. A composition comprising one or more mature, post-translationally-modifed human α-Gal A glycoforms, purified to at least 98% homogeneity and having a specific activity of at least $2.0 \times 10^6$ units/mg protein, wherein the composition comprises greater than 50% complex glycans per α-Gal A glycoforms, produced by separating the α-Gal A glycoforms in a sample from the other components in the sample using a purification procedure selected from the group consisting of: chromatofocusing chromatography, metal chelate affinity chromatography, and immunoaffinity chromatography.

18. The composition of claim 17, wherein at least 67% of the total glycans of said preparation are complex-type glycans.

19. The composition of claim 17, wherein the composition comprises an average of two complex glycans per α-Gal A monomer.

20. A composition comprising one or more mature, post-translationally-modifed human α-Gal A glycoforms with increased oligosaccharide charge, purified to at least 98% homogeneity and having a specific activity of at least $2.0 \times 10^6$ units/mg protein, wherein the composition comprises greater than 50% complex glycans per α-Gal A glycoform, said composition produced by the following steps:

(a) introducing a polynucleotide which, upon expression encodes sialyl transferase, into an α-Gal A-producing cell or introducing a regulatory sequence by homologous recombination that regulates expression of an endogenous sialyl transferase;

(b) culturing the α-Gal A-producing cell under conditions which result in the expression of α-Gal A and sialyl transferase; and (c) isolating the α-Gal A protein, wherein the α-Gal A protein has increased oligosaccharide charge, as compared to α-Gal A produced in a cell without the polynucleotide.

21. The composition of claim 20, wherein at least 67% of the total glycans of said preparation are complex-type glycans.

22. The composition of claim 20, wherein the composition comprises an average of two complex glycans per α-Gal A monomer.

23. A human α-Gal A glycoprotein preparation, produced by the process of:

(a) providing a human cell genetically modified to express an α-Gal A polypeptide; and (b) purifying the α-Gal A polypeptide from the human cell or a culture medium of the human cell;

wherein at least 67% of the total glycans of said preparation are complex-type glycans.

24. A human α-Gal A glycoprotein preparation, produced by the process of:

(a) providing a human cell genetically modified to express an α-Gal A polypeptide; and (b) purifying the α-Gal A polypeptide from the human cell or a culture medium of the human cell;

wherein the preparation comprises an average of two complex glycans per α-Gal A monomer.

25. A human α-Gal A glycoprotein preparation, produced by the process of:

(a) providing a human cell genetically modified to express an α-Gal A polypeptide; and (b) purifying the α-Gal A polypeptide from the human cell or a culture medium of the human cell;

wherein more than 50% of the total glycans of the α-Gal A glycoforms are sialylated.

26. A composition comprising one or more mature, post-translationally-modifed human α-Gal A glycoforms, purified to at least 98% homogeneity and having a specific activity of at least $2.0 \times 10^6$ units/mg protein, wherein the composition comprises greater than 50% complex glycans per α-Gal A glycoform, covalently-conjugated to polyethylene glycol (PEG), wherein the PEG is covalently-conjugated to the α-Gal A glycoforms at one or more sites selected from the group consisting of: amino groups, carboxyl groups, sulfhydryl groups, and carbohydrate groups.

* * * * *

UNITED STATES PATENT AND TRADEMARK OFFICE
CERTIFICATE OF CORRECTION

PATENT NO. : 6,458,574 B1
DATED : October 1, 2002
INVENTOR(S) : Richard F. Selden et al.

It is certified that error appears in the above-identified patent and that said Letters Patent is hereby corrected as shown below:

Title page,
Item [54], Title, "TREATMENT OF A α-GLALACTOSIDASE A DEFICIENCY" Should be -- TREATMENT OF α-GALACTOSIDASE A DEFICIENCY --.
Item [63], Related U.S. Application Data, "Continuation-in-part of application No. 08/928,881, filed on Sep. 12, 1996," should be -- Continuation-in-part of application No. 08/928,881, filed on Sep. 12, 1997, --.
Item [56], References Cited, OTHER PUBLICATIONS, "Herment in et al.,", should be -- Hermentin et al. --; and "Sburlati et al., reference, "Biotechnical", should be -- Biotechnol --.

Column 1,
Line 6, "Sep. 12, 1996," should be -- Sep. 12, 1997, --.
Line 57, "N-6-aininohexanoyl-α-D-galactosylamine" should be -- N-6-aminohexanoyl-α-D-galactosylamine --.

Column 5,
Line 12, "a2,3-sialyl" should be -- α2,3-sialyl --.

Column 10,
Line 19, "cells;" should be -- cells, --.
Line 30, "patents" should be -- patients --.

Column 12,
Line 52, ".Gal" should be -- αGal --.
Line 60, "Sepharose(®" should be -- Sepharose® --.

Column 13,
Line 8, "axial A" should be -- α-Gal --.
Line 21, "Prepg" should be -- Prep® --.

Columns 15 and 16,
Table 1 (throughout ), "Nac" should be -- NAc --.

UNITED STATES PATENT AND TRADEMARK OFFICE
CERTIFICATE OF CORRECTION

PATENT NO. : 6,458,574 B1
DATED : October 1, 2002
INVENTOR(S) : Richard F. Selden et al.

It is certified that error appears in the above-identified patent and that said Letters Patent is hereby corrected as shown below:

Column 18,
Line 10, "(such as Q-Sepharose® " should be -- (such as Q-Sepharose®) --.

Column 20,
Line 43, "cancause" should be -- can cause --.

Column 24,
Line 12, "$_rOSO_2$" should be -- $rOSO_2$ --.

Column 25,
Line 66, "above can administered" should be -- above can be administered --.

Column 28,
Line 20, "0. 1-5.0" should be -- 0.1-5.0 --.

Column 29,
Line 21, "u:-galactosidase" should be -- α-galactosidase --.
Line 46, insert -- 1.1 -- before "Cloning".

Column 33,
Line 7, "BamHII" should be -- BamHI --.

Column 34,
Line 34, "the solution." should be -- the substrate solution. --.

Column 36,
Line 66, "Sepharose(®" should be -- Sepharose®" --.

Column 37,
Line 18, "(x-gal" should be -- α-Gal --.
Line 61, "Superdex(V-200" should be -- Superdex®-200 --.

UNITED STATES PATENT AND TRADEMARK OFFICE
CERTIFICATE OF CORRECTION

PATENT NO. : 6,458,574 B1
DATED : October 1, 2002
INVENTOR(S) : Richard F. Selden et al.

It is certified that error appears in the above-identified patent and that said Letters Patent is hereby corrected as shown below:

<u>Column 57,</u>
Lines 14, 34 and 51,"translationally-modifed" should be -- translationally-modified --.

<u>Column 58,</u>
Line 47, "translationally-modifed" should be -- translationally-modified --.

Signed and Sealed this

Seventeenth Day of August, 2004

JON W. DUDAS
*Acting Director of the United States Patent and Trademark Office*